US012611483B2

(12) United States Patent
Kaufmann et al.

(10) Patent No.: US 12,611,483 B2
(45) Date of Patent: Apr. 28, 2026

(54) IMPLANT COMPRISING A PLURALITY OF HARDENING STATES

(71) Applicant: SetBone Medical Ltd., Ness Ziona (IL)

(72) Inventors: Royi Kaufmann, Hod-HaSharon (IL); Nimrod Kaufmann, Modi'in-Maccabim-Re'ut (IL)

(73) Assignee: SetBone Medical Ltd., Ness Ziona (IL)

( * ) Notice: Subject to any disclaimer, the term of this patent is extended or adjusted under 35 U.S.C. 154(b) by 949 days.

(21) Appl. No.: 17/632,528

(22) PCT Filed: Aug. 25, 2020

(86) PCT No.: PCT/IL2020/050928

§ 371 (c)(1),
(2) Date: Feb. 3, 2022

(87) PCT Pub. No.: WO2021/038562

PCT Pub. Date: Mar. 4, 2021

(65) Prior Publication Data

US 2022/0288272 A1 Sep. 15, 2022

Related U.S. Application Data

(60) Provisional application No. 62/891,460, filed on Aug. 26, 2019.

(51) Int. Cl.
*A61L 24/02* (2006.01)
*A61L 24/00* (2006.01)
(Continued)

(52) U.S. Cl.
CPC ............. *A61L 27/16* (2013.01); *A61L 27/502* (2013.01); *A61L 27/54* (2013.01); *B33Y 80/00* (2014.12); *A61L 2430/38* (2013.01)

(58) Field of Classification Search
None
See application file for complete search history.

(56) References Cited

U.S. PATENT DOCUMENTS

2005/0271727 A1 12/2005 Yao
2005/0277577 A1* 12/2005 Hunter .................. A61K 45/06
424/85.1

(Continued)

FOREIGN PATENT DOCUMENTS

CA 2603773 A1 * 11/2006 ............. A61P 43/00
CN 1419656 5/2003

(Continued)

OTHER PUBLICATIONS

Notification of Office Action and Search Report Dated Dec. 6, 2023 From the National Intellectual Property Administration of the People's Republic of China Re. Application No. 202080068787.9 and Its Machine Translation and Summary Into English. (24 Pages).

(Continued)

*Primary Examiner* — Ann Hu

(57) ABSTRACT

The present invention relates to a deformable body formed of at least 20% by volume of a polymer material in which individual polymer backbones have a plurality of functional groups capable of cross-linking to form a cross-link; said polymer material provided in a first less-cross-linked configuration; wherein said polymer material, upon application of a suitable stimuli, said stimuli causes cross-linking of said functional groups to form cross-linking between said polymer backbones such that said polymer material is in a second more-crosslinked configuration.

21 Claims, 18 Drawing Sheets

(51) Int. Cl.

| | |
|---|---|
| ***A61L 27/16*** | (2006.01) |
| ***A61L 27/50*** | (2006.01) |
| ***A61L 27/54*** | (2006.01) |
| ***B33Y 80/00*** | (2015.01) |

(56) References Cited

U.S. PATENT DOCUMENTS

| | | | | |
|---|---|---|---|---|
| 2009/0270527 | A1* | 10/2009 | Lin | A61L 24/046 523/116 |
| 2010/0272649 | A1* | 10/2010 | Nies | A61P 19/00 424/9.4 |
| 2013/0197126 | A1* | 8/2013 | Vogt | A61L 27/16 523/116 |
| 2017/0348457 | A1* | 12/2017 | Vogt | A61L 24/043 |
| 2024/0366830 | A1 | 11/2024 | Kaufmann et al. | |

FOREIGN PATENT DOCUMENTS

| | | | | | |
|---|---|---|---|---|---|
| CN | 1842350 | | | 10/2006 | |
| CN | 102573944 | A | | 7/2012 | |
| CN | 103223188 | | | 7/2013 | |
| CN | 107569715 | | | 1/2018 | |
| CN | 107569715 | A | * | 1/2018 | C08K 5/14 |
| CN | 114209872 | | | 3/2021 | |
| JP | 2004524111 | A | * | 8/2004 | A61F 2/1616 |
| JP | 2013-240582 | | | 12/2013 | |
| WO | WO 01/71392 | | | 9/2001 | |
| WO | WO 2018/185770 | | | 10/2018 | |
| WO | WO-2018185770 | A1 | * | 10/2018 | A61L 27/18 |
| WO | WO 2021/038562 | | | 3/2021 | |
| WO | WO-2021038562 | A1 | * | 3/2021 | B33Y 80/00 |
| WO | WO 2023/053119 | | | 4/2023 | |

OTHER PUBLICATIONS

International Search Report and the Written Opinion Dated Jan. 15, 2023 From the International Searching Authority Re. Application No. PCT/IL2022/051032. (10 Pages).

Decision on Rejection Dated Apr. 26, 2023 From the State Intellectual Property Office of the People's Republic of China Re. Application No. 202080068787.9. (5 Pages).

Translation Dated Feb. 17, 2023 of Notification of Office Action Dated Feb. 12, 2023 From the State Intellectual Property Office of the People's Republic of China Re. Application No. 202080068787.9. (6 pages).

International Preliminary Report on Patentability Dated Mar. 10, 2022 From the International Bureau of WIPO Re. Application No. PCT/IL2020/050928. (9 Pages).

International Search Report and the Written Opinion Dated Dec. 1, 2020 From the International Searching Authority Re. Application No. PCT/IL2020/050928. (14 Pages).

Notification of Office Action and Search Report Dated Jul. 28, 2022 From the State Intellectual Property Office of the People's Republic of China Re. Application No. 202080068787.9 and Its Translation of Office Action Into English. (10 Pages).

International Preliminary Report on Patentability Dated Apr. 11, 2024 From the International Bureau of WIPO Re. Application No. PCT/IL2022/051032 (8 Pages).

Notification of Office Action Dated Feb. 12, 2023 From the State Intellectual Property Office of the People's Republic of China Re. Application No. 202080068787.9. (5 Pages).

Communication Pursuant to Article 94(3) EPC Dated Aug. 16, 2023 From the European Patent Office Re. Application No. 20772445.1 (6 Pages).

Notice of Reasons for Rejection Dated Oct. 22, 2024 From the Japan Patent Office Re. Application No. 2022-512399 and its Translation Into English. (8 Pages).

English Summary Dated Apr. 28, 2023 of Decision on Rejection Dated Apr. 26, 2023 From the State Intellectual Property Office of the People's Republic of China Re. Application No. 202080068787.9. (2 pages).

Decision on Rejection Dated May 29, 2024 From the State Intellectual Property Office of the People's Republic of China Re. Application No. 202080068787.9 and Its Machine Translation Into English. (13 Pages).

Summary of Decision on Rejection Dated May 29, 2024 From the State Intellectual Property Office of the People's Republic of China Re. Application No. 202080068787.9. (4 Pages).

Notice of Reasons for Rejection Dated Jun. 10, 2025 From the Japan Patent Office Re Application No. 2022-512399 and its Machine Translation into English. (4 Pages).

Supplementary European Search Report and the European Search Opinion Dated Jun. 24, 2025 From the European Patent Office Re. Application No. 22875325.7. (9 Pages).

Communication Pursuant to Article 94(3) EPC Dated Oct. 8, 2025 From the European Patent Office Re. Application No. 20772445.1 (6 Pages).

* cited by examiner

Pv-GMA polymer

Bis-GMA methacrylic resin

PVA + GMA → Pv-GMA

Pv-GMA-GAE

Pv-GMA-GAE

PVA GAE Pv-GAE

Glycidyl butyl ether

Glycidyl tert-butyl ether

PVA Alkyl Halide Pv-AE

Butyl chloride

Load empty cartridges 716 into the device, inside the temperature-controlled chamber 708

Rotation of mixing blades 704 mixes the material inside the cartridges 716 while inside the temperature-controlled chamber 708

Nitrogen inlets 706 deliver nitrogen into the lower end of cartridges 716 during the mixing process while inside the temperature-controlled chamber 708

IMPLANT COMPRISING A PLURALITY OF HARDENING STATES

RELATED APPLICATIONS

This application is a National Phase of PCT Patent Application No. PCT/IL2020/050928 having International filing date of Aug. 25, 2020, which claims the benefit of priority under 35 USC § 119 (e) of U.S. Provisional Patent Application No. 62/891,460 filed on Aug. 26, 2019. The contents of the above applications are all incorporated by reference as if fully set forth herein in their entirety.

FIELD AND BACKGROUND OF THE INVENTION

The present invention, in some embodiments thereof, relates to medical grade and non-medical grade materials, which are configured to change their property following stimulation.

Bone fractures are caused by high force impact or stress, where the fracture is then properly termed a traumatic fracture, or as by certain medical conditions that weaken the bones, such as osteoporosis, metastatic bone disease, or osteogenesis imperfecta, where the fracture is then properly termed a pathologic fracture.

A common surgery procedure to treat bone fractions comprises in the use of orthopedic implants for replacing or supplementing or augmentation of the fractured or degenerated bone. Numerous types of biocompatible orthopedic implants are available. Some are made of solid metals, such as stainless steel, cobalt-chromium-molybdenum alloy, tungsten, titanium, cobalt-chromium-tungsten-nickel, and similar alloys. Others are made of solid polymers compounds such as polyetheretherketone (PEEK). Some orthopedic implants are also made of ceramics or composite materials.

U.S. Pat. No. 5,264,215A discloses "a bone cement composition comprising polyalkyl methacrylate derived from methacrylate having an alkyl group of 1-4 carbon atoms, hydroxyapatite, alkyl methacrylate having an alkyl group of 1-4 carbon atoms, 4-(2-methacryloyloxyethyl)trimellitic acid or anhydride thereof, and a polymerization initiator. Also disclosed are a cured product of the composition, an implant material using the composition and a process for the preparation of the implant material".

U.S. Pat. No. 5,538,514A discloses "a method for molding bone cement to a prosthetic implant in which a cement mixture absent any amine initiators is molded about the implant and polymerization is initiated by exposing the cement mixture to a radiation source. The method eliminates the manufacturing timing problems of molding a polymerizing bone cement mixture to an implant".

U.S. Pat. No. 8,475,536B2 discloses "Biomedical implants (e.g., orthopedic implants) with modified surfaces that can enhance a cement bond's strength (e.g., tensile, shear, and/or fatigue) are disclosed, along with methods of manufacturing and using such implants. The implants can exhibit a variety of physical, chemical, or process-derived features which can enhance cement bonding. For instance, the implant surface can exhibit particular roughness values, and/or be substantially free of non native material. Processes for producing such implants can include providing a first roughened implant surface, which can be produced, for example, by particle blasting. A treatment formulation can be applied to the first roughened surface to create a second roughened surface that exhibits enhanced cement bonding properties relative to the first roughened surface. In some instances, the first roughened surface and the second roughened surface can exhibit substantially similar Ra values. The second roughened surface can exhibit a negative Rsk value."

U.S. Pat. No. 8,926,710B2 discloses "osteoconductive bone graft materials. These compositions contain injectable cements and demineralized bone matrix fibers. The combination of these materials enables the filling of a bone void while balancing strength and resorption".

U.S. Pat. No. 8,834,845B2 discloses "a bioactive PMMA (polymethylmethacrylate) bone cement contains a powder component and a reactive monomer liquid, wherein the powder component and the reactive monomer liquid when mixed with one another react with one another and form a polymer-based solid material. The powder component contains particulate polymer powder of polymethylmethacrylates; a radical starter; and anionic copolymer nanoparticles. The anionic copolymer nanoparticles are distributed in nano-particulate form within the particulate powder component or coated as a film on particles of the particulate polymer powder".

SUMMARY OF THE INVENTION

According to an aspect of some embodiments of the present invention there is provided a medical grade implant, comprising a deformable body formed of at least 20% by volume of a polymer material in which individual polymer backbones have a plurality of functional groups capable of cross-linking to form a cross-link; said polymer material provided in a first less-cross-linked configuration; wherein said polymer material, upon application of a suitable stimuli, said stimuli causes cross-linking of said functional groups to form cross-linking between said polymer backbones such that said polymer material is in a second more-cross-linked configuration.

According to some embodiments of the invention, said first less-cross-linked configuration comprises from about 0.1% of cross-links to about 1% of cross-links.

According to some embodiments of the invention, said second more-cross-linked configuration comprises from about 50% of cross-links to about 90% of cross-links.

According to some embodiments of the invention, the polymer comprises methacrylate groups covalently attached to polyvinyl alcohol (PVA).

According to some embodiments of the invention, said functional groups comprise methacrylate and said polymer backbones comprise PVA.

According to some embodiments of the invention, the polymer is selected from the group consisting of Pv-GMA, Pv-IMA, Pv-AMA, Pv-EMA, Pv-MA or any combination thereof.

According to some embodiments of the invention, the medical grade implant further comprising at least one additive that makes said implant sensitive to said stimuli.

According to some embodiments of the invention, said polymer comprises less than 10% of free monomers.

According to some embodiments of the invention, said polymer comprises no free monomers.

According to some embodiments of the invention, said implant comprises less than 10% by volume of said polymer material.

According to some embodiments of the invention, said implant comprises more than 80% by volume of said polymer material.

According to some embodiments of the invention, said implant comprises from about 60% to about 90% by volume of said polymer material.

According to some embodiments of the invention, in said first less-cross-linked configuration said implant has an elastic modulus from about 0.01 to about 1 MPa.

According to some embodiments of the invention, in said second more-cross-linked configuration said device has an elastic modulus from about 2 to about 500 MPa.

According to some embodiments of the invention, said elastic modulus changes from said first less-cross-linked configuration to said second more-cross-linked configuration by a factor from about 10 to about 1000.

According to some embodiments of the invention, an average molecular weight of said polymer is from about 10,000 to about 200,000 g/mol.

According to some embodiments of the invention, an average molecular weight of said polymer is from about 1,000 to about 200,000 g/mol.

According to some embodiments of the invention, a natural heat of a patient is suitable to act as said stimuli.

According to some embodiments of the invention, said functional groups are active functional groups.

According to some embodiments of the invention, said cross-linking of said functional groups is cross-linking with each other.

According to some embodiments of the invention, said cross-linking of said functional groups is cross-linking with another material included in said implant.

According to some embodiments of the invention, said at least one additive makes said polymer material sensitive to one or more of light, UV Vis, a temperature above a temperature threshold, IR and any combination thereof.

According to some embodiments of the invention, the time required for said stimuli to finish 80% of the cross-linking is from about 1 minutes to about 30 minutes.

According to some embodiments of the invention, said temperature threshold is above 20 degrees Celsius.

According to some embodiments of the invention, the time required for said UV to finish 80% of the cross-linking is from about 2 seconds to about 20 minutes.

According to some embodiments of the invention, said stimuli is a small molecule.

According to some embodiments of the invention, said implant is made of biocompatible materials.

According to some embodiments of the invention, the cross-linking from said first less-cross-linked configuration to said second more-cross-linked configuration comprises a non-uniform cross-linking of said functional groups with each other.

According to some embodiments of the invention, the cross-linking from said first less-cross-linked configuration to said second more-cross-linked configuration comprises a non-uniform change of elastic modulus in said implant.

According to some embodiments of the invention, the cross-linking from said first less-cross-linked configuration to said second more-cross-linked configuration comprises a non-uniform cross-linking location within said implant.

According to some embodiments of the invention, the cross-linking from said first less-cross-linked configuration to said second more-cross-linked configuration comprises a biocompatible cross-linking process.

According to some embodiments of the invention, said deformable body comprises at least one pharmacological agent.

According to some embodiments of the invention, said deformable body comprises at least one additional radiopaque marker additive.

According to an aspect of some embodiments of the present invention there is provided a curable medical grade implant, wherein said implant comprises at least one deformable portion, said deformable portion comprises at least 20% by volume of Pv-GMA, Pv-IMA, Pv-AMA, Pv-EMA, Pv-MA or any combination thereof.

According to some embodiments of the invention, said at least one deformable portion is from about 1% to about 25% of an internal or external plasticizer.

According to some embodiments of the invention, said at least one deformable portion is more than 80% of said curable medical grade implant.

According to some embodiments of the invention, said at least one deformable portion is less than 50% of said curable medical grade implant.

According to some embodiments of the invention, said at least one deformable portion is from about 10% to about 90% of said curable medical grade implant.

According to some embodiments of the invention, a non-deformable portion of said implant is made of medical grade steel.

According to an aspect of some embodiments of the present invention there is provided a method to treat a tissue of a patient, comprising:

a. delivering at least one medical grade implant to the targeted tissue; and
b. stimulating said at least one implant to cause cross-linking the body of said at least one implant from a first configuration to a second configuration;

wherein said stimulating is performed by the natural heat of the body of said patient.

According to an aspect of some embodiments of the present invention there is provided a medical grade implant system, comprising:

a. a deformable body formed of at least 20% by volume of a polymer material in which individual polymer backbones have a plurality of functional groups capable of cross-linking to form a cross-link; said polymer material provided in a first less-cross-linked configuration; at least one additive that makes said implant sensitive to a suitable stimuli; wherein said polymer material, upon application of said suitable stimuli, said suitable stimuli causes cross-linking of said functional groups to form cross-linking between said polymer backbones such that said polymer material is in a second more-cross-linked configuration; and
b. a medical grade implant delivery device.

According to some embodiments of the invention, optionally comprising at least one means to provide stimuli.

According to some embodiments of the invention, said at least one additive makes said polymer material sensitive to one or more of light, UV Vis, a temperature above a temperature threshold, IR, water, pH and any combination thereof.

According to an aspect of some embodiments of the present invention there is provided a medical grade implant kit, comprising:

a. a deformable body formed of at least 20% by volume of a polymer material in which individual polymer backbones have a plurality of functional groups capable of cross-linking to form a cross-link; said polymer material provided in a first less-cross-linked configuration; at least one additive that makes said implant sensitive to a suitable stimuli; wherein said polymer material, upon application of said suitable stimuli, said suitable stimuli causes cross-linking of said functional groups to form cross-linking between said polymer backbones such that said polymer material is in a second more-cross-linked configuration; and b. a medical grade implant delivery device.

According to an aspect of some embodiments of the present invention there is provided a deformable body formed of polymer comprising a deformable body formed of at least 20% by volume of a polymer material in which individual polymer backbones have a plurality of functional groups capable of cross-linking to form a cross-link; said polymer material provided in a first less-cross-linked configuration; at least one additive that makes said deformable body sensitive to a suitable stimuli; wherein said polymer material, upon application of said suitable stimuli, said suitable stimuli causes cross-linking of said functional groups to form cross-linking between said polymer backbones such that said polymer material is in a second more-cross-linked configuration.

According to an aspect of some embodiments of the present invention there is provided a non-medical grade implant, comprising a deformable body formed of at least 20% by volume of a polymer material in which individual polymer backbones have a plurality of functional groups capable of cross-linking to form a cross-link; said polymer material provided in a first less-cross-linked configuration; at least one additive that makes said implant sensitive to a suitable stimuli; wherein said polymer material, upon application of said suitable stimuli, said suitable stimuli causes cross-linking of said functional groups to form cross-linking between said polymer backbones such that said polymer material is in a second more-cross-linked configuration.

According to an aspect of some embodiments of the present invention there is provided the use of a material for medical grade implants comprising a deformable body formed of at least 20% by volume of a polymer material in which individual polymer backbones have a plurality of functional groups capable of cross-linking to form a cross-link; said polymer material provided in a first less-cross-linked configuration; at least one additive that makes said deformable body sensitive to a suitable stimuli; wherein said polymer material, upon application of said suitable stimuli, said suitable stimuli causes cross-linking of said functional groups to form cross-linking between said polymer backbones such that said polymer material is in a second more-cross-linked configuration.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Overview

Figure 1:
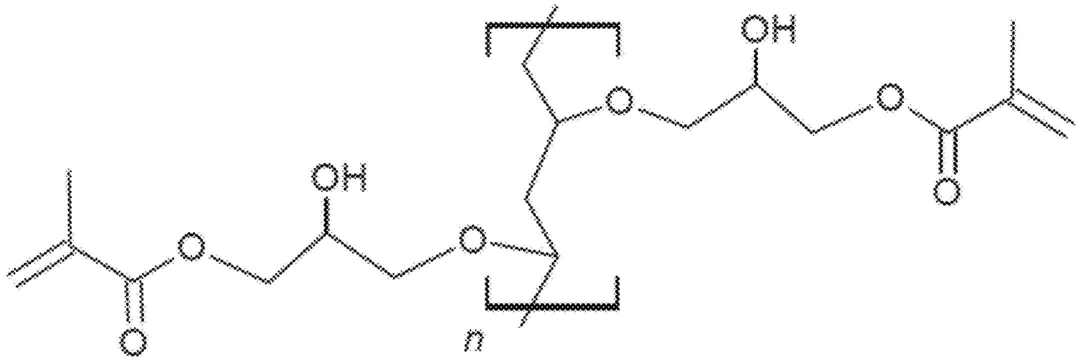
FIG. 1 is a schematic illustration showing a comparison between the Pv-GMA polymer and a common Bis-GMA methacrylic resin, according to some embodiments of the present invention.
Figure 1:
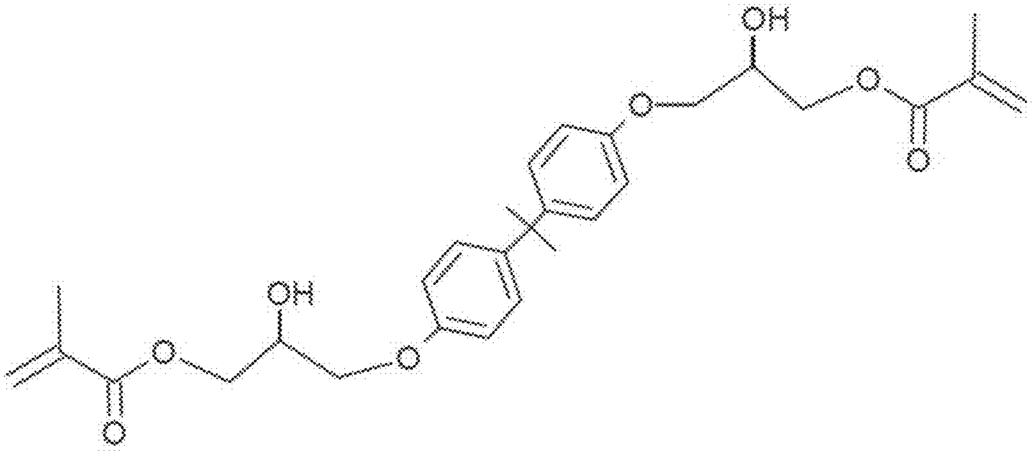

An aspect of some embodiments of the present invention relates to orthopedic implants comprising several hardening states, from soft to hard, in which the changes between hardening states are initiated by the temperature of the body of the patient. In some embodiments, the changes between hardening states are controllable by the user. In some embodiments, controlling the hardening states is done by controlling the temperature near the implant. In some embodiments, controlling the hardening states is done by controlling the stimuli. In some embodiments, controlling the hardening states is done by controlling the materials of the implant. In some embodiments, the changes between hardening states are reversible, for example by hydrolysis (e.g.: acid or base hydrolysis) of an ester bond formed in the GMA upon hardening. In some embodiments, the changes between hardening states are irreversible. In some embodiments, the temperature of the body of the patient provides enough heat to completely finish the process of curing in the orthopedic implant. In some embodiments, light, UV Vis, water, pH or IR, is used for curing the implant.

An aspect of some embodiments of the present invention relates to orthopedic implants that comprise two levels of solid state, one being a flexible and/or malleable and/or modifiable solid state and the other being a non-flexible solid state. In some embodiments, the orthopedic implant is kept in its flexible and/or malleable and/or modifiable solid state until is it necessary. In some embodiments, the orthopedic implant is kept in its flexible and/or malleable and/or modifiable solid state by keeping the device at low temperatures. In some embodiments, low temperatures are lower than 30 degrees Celsius.

An aspect of some embodiments of the present invention relates to orthopedic implants comprising a backbone polymer and a plurality of active Methacrylate (MA) molecules. In some embodiments, the backbone is a polyvinyl alcohol polymer. In some embodiments, more than 80% of the chains of the backbone comprise covalently bonded Methacrylate (MA) molecules. In some embodiments, the final orthopedic implant does not comprise free monomers.

An aspect of some embodiments of the present invention relates to orthopedic implants that are ready to use and/or do not require preliminary actions before their use, for example, mixing of raw materials and/or mixing of powders and liquids. In some embodiments, the orthopedic implant comprises one single polymer and an initiator, already mixed in a dedicated container and ready to be used. In some embodiments, the initiator is a thermal initiator, which allows the orthopedic implant to polymerize at body temperatures. In some embodiments, the initiator is covalently bond to the chain. In some embodiments, the orthopedic implant comprise a mix of viscous liquid or paste polymer with liquid or paste initiator. In some embodiments, the mixing is a self-mixing, which is achieved during the delivery (for example injection) process.

An aspect of some embodiments of the invention relates to providing a medical grade curable implant comprising a plurality of controllable solid states. In some embodiments, the control over the solid states is performed by changing the temperature that the implant is exposed. In some embodiments, the phases of solid state are one or more of reversibly solid state, flexible and stretchable amorphous semi-liquid state and irreversibly solid state. In some embodiments, the reversibly solid state is kept like that when said curable medical grade implant is kept at a temperature below 25° C. In some embodiments, the flexible and stretchable amorphous semi-liquid state is kept like that when said curable medical grade implant is kept at a temperature between about 25° C. and about 37° C. In some embodiments, the irreversibly solid state is activated when said curable medical grade implant is exposed to a temperature above 37° C. In some embodiments, the controllable solid states are enabled by the addition of one or more plasticizers.

An aspect of some embodiments of the invention relates to providing a medical grade curable implant that during the curing process there is minimum production of bubbles that might weaken the implant. In some embodiments, reduction of creation of bubbles is enabled by the addition of plasticizers to the materials of the implant. In some embodiments, reduction of creation of bubbles is enabled by modifying the viscosity of the implant by the addition of the plasticizers. In some embodiments, modification of viscosity is a reduction of from about 10% to about 50%.

An aspect of some embodiments of the invention relates to providing a medical grade curable implant with an increased shelf life. In some embodiments, shelf life is increased by providing the implant with stable solid states that allow the long-term shelving of the implant. In some embodiments, stable solid states are achieved by the addition of plasticizers to the materials of the implant. In some embodiments, shelf life of the implant is from about one year to about 50 years.

An aspect of some embodiments of the present invention relates to orthopedic implants that after the curing process the final volume increases from about 0.1% to about 5%, in relation to the volume before the curing process.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

In some embodiments, "medical grade" refers to a material which is within the standards of the different countries, international associations, etc. (e.g. FDA, ASTM, ISO, etc.).

In some embodiments, the terms "implant", "implants", "medical grade implants" and "medical implant", are interchangeable.

General Exemplary Implant

In some embodiments, implants disclosed herein are curable to a hardened form by application of an initiating energy. In some embodiments, the initiating energy is heat, and, in some embodiments, the source of the heat is the natural body heat of the patient.

In some embodiments, a variety of hardening mechanisms can be utilized, depending upon material selection, including for example, curing that is initiated by polymers, cross-linkers, ultraviolet radiation, visible light, infrared radiation, radio frequency radiation, X-ray radiation, gamma radiation, or other wavelength of electromagnetic energy, catalyst-initiated polymerization, thermally-initiated polymerization, electrically-initiated polymerization, mechanically-initiated polymerization, curing initiated by electron beam radiation and the like.

In some embodiments, medical grade implants containing a pre-made or semi pre-made hardenable material, and that are configured to be hardened after placement in a desired in vivo position by application of a cure-initiating energy, may find advantageous use in a variety of different circumstances. For example and without limitation, such implants can be used in circumstances in which it is desirable for medical personnel to work with a medical implant with no risk of leakage, to work with a medical implant adapted to be accurately placed in the body of the subject and/or to work with a medical implant that do not require time consuming preparations. Furthermore, in some embodiments, such implants can be used in circumstances in which it is desirable for medical personnel to work with a medical implant that does not change its properties before placed at target site or triggered by medical personnel. Hence, the medical personnel is not limited to a specific and/or short in implantation time-window. In addition, in some embodiments, the invention provides a medical grade implant as disclosed above that during the curation process there is little to none creation of bubbles inside the medical grade implant. In addition, in some embodiments, the invention provides a medical grade implant that comprises a level of viscosity that allows easy injection of the curable material in the elected place. In some embodiments, the viscosity (dynamic viscosity) of the material is from about 1000 Pa*s to about 500 Pa*s. Optionally from about 1500 Pa*s to about 300 Pa*s. Optionally from about 2000 Pa*s to about 200 Pa*s. In addition, in some embodiments, the invention provides a medical grade implant with an extended shelf life with little to none danger of losing effectivity during the time in the shelf. In some embodiments, the extended shelf life is from about 1 year to about 5 years. Optionally from about 5 years to about 10 years. Optionally from about 10 years to about 100 years.

In some embodiments, the versatility also allows for a less invasive technique for orthopedic implantation procedures, allows for a greater design flexibility with regard to the implant device, and enables the avoidance or reduction of complications that can arise during a wet out mixing process during surgery. The embodiments are described primarily by reference to bone devices; however, it is intended that the application be understood to encompass medical devices used in other locations, and non-medical devices used in different scenarios (e.g. construction, arts, etc.) as well.

In some embodiments, the invention relates to a medical grade implant. In some embodiments, the invention relates to a medical grade implant system. In some embodiments, the invention relates to a medical grade implant kit. In some embodiments, the invention relates to a medical grade implant delivery device. In some embodiments, the invention relates to a medical grade biocompatible implant initiator. In some embodiments, the invention relates to materials for non-medical applications. In some embodiments, the invention relates to any combination of the abovementioned.

In some embodiments, the orthopedic implants comprise at least one type polymer. In some embodiments, the orthopedic implants comprise a chain of monomers bound one directly to another. In some embodiments, binding of monomers are performed allowing at least one group active. In some embodiments, the orthopedic implants comprise at least one type polymer and no free monomers in the final product. In some embodiments, the orthopedic implants comprise at least one type polymer and at least one type of functional group. In some embodiments, the implant comprises several states of elasticity. In some embodiments, the changes in the states of elasticity are controlled by the user. In some embodiments, the changes in the states of elasticity are reversible. In some embodiments, the changes in the states of elasticity are irreversible. In some embodiments, the changes in the variety of states are initiated by a trigger and/or an initiator. In some embodiments, each at least one type of functional group attached to at least one binding site of the at least one type of polymer. In some embodiments, each at least one type of functional group is attached to at least two or at least three binding sites of said at least one type of polymer. In some embodiments, the at least one type of functional group is connected on a first side to the at least one type of polymer, and is connected on a second side to another at least one type of functional group and/or to another at least one type of polymer.

In some embodiments, the orthopedic implants are inserted into the body of a patient through narrow passages and the implant fills voids larger than the narrow passage. In some embodiments, the orthopedic implant comprises pores, no larger than the size of micropores.

In some embodiments, the orthopedic implant is characterized by a variety of sizes and shapes. In some embodiments, the shapes can be any geometrical form. In some embodiments, the size is from about 1 millimeter square to about 1000 centimeter square. In some embodiments, the orthopedic implant is arranged in strips having sizes, for example, of 2*2*200 mm, optionally larger sizes, optionally smaller sizes.

In some embodiments, the orthopedic implants can be assembled into orthopedic implant kits consisting of bone augmentation material alone without the need for further compound that allows the curing of the bone augmentation material. In some embodiments, the device is designed to contain the implant components and deliver the implant to the target site, optionally, via a minimally invasive procedure.

In some embodiments, the implant is solid and amorphous, having elastic property and uncured. In some embodiments, the implant material is inserted into a delivery tube. In some embodiments, the delivery tube further comprises an anti-friction compound. In some embodiments, a delivery device consists of the delivery tube and means to eject the bone augmentation material through the delivery tube outlet. In some embodiments, while the bone augmentation material is ejected out of the delivery tube, it receives the form of the area into which is being injected.

In some embodiments, during an orthopedic procedure e.g. treating fractured bone, the delivery device is inserted to the target site, e.g. a fractured vertebra. In some embodiments, the procedure is optionally done in a minimally invasive procedure, optionally by inserting the delivery tube through a cannula. In some embodiments, the delivery device is then activated to release the bone augmentation material. In some embodiments, the bone augmentation material that is released out of the delivery tube occupies the space into it is being ejected. In some embodiments, the implant released out of the delivery device absorbs the natural body heat, optionally, until is fully cured. In some embodiments, the bone augmentation material is cured at the target site, forming a solid implant, adapted to the shape of the space in which was injected.

In some embodiments, the bone augmentation material reduces the risk of material leakage. In some embodiments, the combination of bone augmentation material and various types of materials with absorption property may result in improved mechanical properties of the implant and/or to promote bone ingrowth.

In some embodiments, the implant is preferably made of a bio-compatible polymer e.g.; poly(methyl acrylate), poly (methyl methacrylate), poly(ethyl methacrylate), polyvinylchloride, polytetrafluoroethylene, polyethersulfone, polyethylene, polyetherketone, polysulfone, polypropylene. In some embodiments, a co-polymer is used. In some embodiments, a combination of different polymers or co-polymers or other bio-compatible materials are used.

In some embodiments, the implant is made of Methacrylate (MA) molecules connected along a carbon chain. In some embodiments, there are no free monomers in the final product. In some embodiments, the implant polymer is mixed with some additives such as initiator molecule, radiopaque molecules, growth factors, pharmaceuticals, chemicals, proteins, and others.

Exemplary Embodiment of an Implant

In some embodiments, the medical implant is configured as a monomers-free methacrylic polymer (also called bone augmentation material in the relevant examples) with two phases of solid state. In some embodiments, at the first phase, the polymer is a flexible and stretchable amorphous solid. In some embodiments, optionally, the polymer can be non or slightly cross-linked. In some embodiments, said slightly cross-linked (also referred to a less-cross-linked configuration) comprises from about 0.1% of cross-links to about 1% of cross-links. In some embodiments, contrary to slightly cross-linked polymer, there is a cross-linked polymer (also referred to a more-cross-linked configuration) which comprises from about 50% of cross-links to about 90% of cross-links. In some embodiments, these properties allow the medical implant to be easily inserted through a narrow hole into a cavity and assume the shape of the cavity. In some embodiments, in case that the target place is accessible, for example in open surgery, the medical implant can be directly placed in the target place.

In some embodiments, the implant comprises a surface texture that allows the implant to be better embedded in the site of implantation.

In some embodiments, the implant can have a predetermined shape. In some embodiments, the implant is cut to the desired shape using regular tools (e.g. scissors, knifes, etc.). In some embodiments, the implant is curated inside external molds and can be implanted in specific sites. For example, this technique can be used to shape bone plates for skulls or shape specific bone fragments.

Exemplary Compositions of Curable Implant

In some embodiments, a curable implant according to any of the respective embodiments described herein comprises a polymer comprising a plurality of active Methacrylate (MA) molecules connected along a carbon chain. In some embodiments, the chain is made by binding one monomer to another directly. Optionally, the binding is performed while also keeping the MA groups active. In some embodiments, the binding is performed by binding the monomers with linking molecules, or by binding the MA monomers onto a backbone polymer. In some embodiments, the medical implant is made by binding Glycidyl methacrylate (GMA) monomers onto a polyvinyl alcohol (PVA) polymer to produce a stable Pv-GMA polymer.

Referring now to FIG. 1, showing a comparison between the Pv-GMA polymer and a common Bis-GMA methacrylic resin. In some embodiments, one difference between a common Bis-GMA methacrylic resin, in which the methacrylic groups are bonded to a Bisphenol-A, is that in the Pv-GMA product the Bisphenol-A is replaced with a biocompatible carbon chain. In some embodiments, more than 80% of the MA groups are bounded and, therefore, there are no free monomers in the product, optionally more than 90%, optionally 100%.

Polymer:

The polymer comprised by the implant (according to any of the respective embodiments described herein) may comprise any suitable polymer known in the art, for example, a biocompatible polymer.

Examples of suitable polymers include, without limitation, poly(vinyl alcohol) (PVA), poly(vinyl acetate) (PVAc), polyvinylamine (PVM), poly(vinyl chloride), fluoropolymers, polyesters, polyurethanes, polyureas, silicones, and copolymers thereof.

Examples of suitable fluoropolymers include, without limitation, polytetrafluoroethylene (PTFE), poly(vinylidene difluoride) (PVDF), polychlorotrifluoroethylene (PCTFE), and poly(vinyl fluoride) (PVF).

In some embodiments of any of the respective embodiments described herein, the polymer is poly(vinyl alcohol) (PVA) of a copolymer thereof, for example, poly(vinyl alcohol-co-ethylene), poly(vinyl alcohol-co-vinyl acetate), poly(vinyl alcohol-co-methyl methacrylate), poly(vinyl alcohol-co-vinyl butyral), poly(vinyl alcohol-co-vinyl chloride), a block copolymer of poly(vinyl alcohol) and poly (ethylene oxide), or a copolymer thereof (e.g., poly(vinyl alcohol-co-vinyl butyral-co-vinyl acetate) or poly(vinyl alcohol-co-vinyl acetate-co-vinyl chloride), which may be regarded as copolymers of poly(vinyl alcohol-co-vinyl acetate) with poly(vinyl alcohol-co-vinyl butyral) or poly (vinyl alcohol-co-vinyl chloride), respectively).

Thus, for example, the polymer optionally comprises one or more species of backbone units, such as, e.g., vinyl alcohol, vinylamine, vinyl chloride, vinyl fluoride, binylidene difluoride, chlorotrifluoroethylene, ethylene, vinyl acetate, methyl methacrylate, vinyl butyral, and/or ethylene oxide backbone units, as this term is defined herein.

In some embodiments any of the respective embodiments described herein, the polymer has a cross-linked polymer having formula I:

$$[X]m[X(-L-Y)]n \qquad \text{Formula (I)}$$

wherein:

- X is a backbone unit which forms a polymeric backbone;
- L is absent or is a linking moiety;
- Y is a cross-linkable functional group according to any of the respective embodiments described herein;
- m is zero or a positive integer, representing an average number of [X] units in a polymeric backbone;
- n is an integer which is at least 1, representing an average number of [X(-L-Y)] units, in a polymeric backbone; wherein the sum of m and n is at least 10 (optionally at least 100 or at least 1,000, and optionally no more than 1,000,000, no more than 100,000 or no more than 10,000).

As used herein, the term "backbone unit" refers to a repeating unit, which optionally comprises a side chain (as defined herein), wherein linkage of a plurality of the repeating unit (e.g., sequential linkage) forms a polymeric backbone, optionally with side chains attached to the backbone.

Herein, the "backbone" of a polymer refers to a chain of atoms which is formed by linking repeating units (backbone units) to one another to form the polymer, further including hydrogen atoms and oxo groups attached to the chain (whereas other groups attached to the chain of atoms are referred to as side chains).

Herein, the phrase "side chain" refers to any group (comprising one or more atoms) other than a hydrogen atom or oxo (=O), which is attached to an atom in the backbone of a polymer.

As shown in formula I, L and Y together form a pendant group of at least a portion of the backbone units, which group is referred to herein for brevity simply as the "pendant group".

Each backbone unit with a pendant group according to any of the respective embodiments described herein (e.g., a unit represented by X(-L-Y) in formula I, the number of which is represented by the variable n), each backbone unit without a pendant group according to any of the respective embodiments described herein (e.g., a unit represented solely by X in formula I, the number of which is represented by the variable m). Thus, a backbone unit refers to a repeating portion of a monomeric unit, which includes (but is not limited to) the portion which forms a polymeric backbone.

A backbone unit according to any of the respective embodiments described herein may optionally be a residue of a polymerizable monomer or polymerizable moiety of a monomer. A wide variety of polymerizable monomers and moieties will be known to the skilled person, and the structure of the residues of such monomers which result upon polymerization (e.g., monomeric units) will also be known to the skilled person.

A "residue of a polymerizable monomer" refers to a modified form of a polymerizable monomer and/or a portion of a polymerizable monomer that remains after polymerization.

A portion of a polymerizable monomer may be formed, for example, by a condensation reaction, e.g., wherein at least one atom or group (e.g., a hydrogen atom or hydroxyl group) in the monomer, and optionally at least two atoms or groups (e.g., a hydrogen atom and a hydroxyl group) in the monomer, is replaced with a covalent bond with another polymerizable monomer.

A modified form of a polymerizable monomer may be formed, for example, by ring-opening (wherein a covalent bond between two atoms in a ring is broken, and the two atoms optionally each become linked to another polymerizable monomer); and/or by adding to an unsaturated bond, wherein an unsaturated bond between two adjacent atoms is broken (e.g., conversion of an unsaturated double bond to a saturated bond, or conversion of an unsaturated triple bond to an unsaturated double bond) and the two atoms optionally each become linked to another polymerizable monomer.

A modified form of a polymerizable monomer may consist essentially of the same atoms as the original monomer, for example, different merely in the rearrangement of covalent bonds, or alternatively, may have a different atomic composition, for example, wherein polymerization includes a condensation reaction (e.g., as described herein).

A modified form of a polymerizable monomer may optionally be modified following polymerization, for example, by cleavage of a side chain. For example, poly (vinyl alcohol) and copolymers thereof are commonly prepared by polymerizing vinyl acetate (because vinyl alcohol per se is not readily polymerizable) to obtain poly)vinyl acetate) or a copolymer thereof, and then some or all of the acetate groups to obtain vinyl alcohol backbone units (optionally in combination with remaining vinyl acetate backbone units). Vinyl alcohol backbone units may also be formed, for example, by (partial or complete) nucleophilic substitution of a side chain (e.g., chloride in a vinyl chloride unit) by hydroxide.

Examples of backbone units include, without limitation, substituted or unsubstituted hydrocarbons (which may form a substituted or unsubstituted hydrocarbon backbone), such as alkylene units; hydroxycarboxylic acid units (which may form a polyester backbone), e.g., glycolate, lactate, hydroxybutyrate, hydroxyvalerate, hydroxycaproate and hydroxybenzoate units; dicarboxylic acid units (which may form a polyester backbone in combination with a diol and/or a polyamide in combination with a diamine), e.g., adipate, succinate, terephthalate and naphthalene dicarboxylic acid units; diol units (which may form a polyether backbone, or form a polyester backbone in combination with a dicarboxylic acid), e.g., ethylene glycol, 1,2-propanediol, 1,3-propanediol, 1,4-butanediol, and bisphenol A units; diamine units (which may form a polyamide backbone in combination with a dicarboxylic acid), e.g., para-phenylene diamine and alkylene diamines such hexylene diamine; carbamate units (which may form a polyurethane backbone); amino acid residues (which may form a polypeptide backbone); and saccharide residues (which may form a polysaccharide backbone).

In some embodiments of any of the embodiments described herein, the polymer comprises backbone units (e.g., X in formula I) which are a substituted or unsubstituted alkylene unit.

In some embodiments, the polymer comprises backbone units (e.g., X in formula I) which are a substituted or unsubstituted ethylene unit, that is, an alkylene unit 2 atoms in length.

Polymers wherein X is a substituted or unsubstituted ethylene unit may optionally comprise a polymeric backbone such as formed by polymerizing ethylene ($CH_2{=}CH_2$) and/or substituted derivatives thereof (also referred to herein as "vinyl monomers"). Such polymerization is a very well-studied procedure, and one of ordinary skill in the art will be aware of numerous techniques for effecting such polymerization.

It is to be understood that any embodiments described herein relating to a polymers formed by a polymerization encompass any polymers having a structure which can be formed by such polymerization, regardless of whether the polymer was formed in practice by such polymerization (or any other type of polymerization).

As is well known in the art, the unsaturated bond of ethylene and substituted ethylene derivatives becomes saturated upon polymerization, such that the carbon bonds in the polymeric backbone are saturated, although they may be referred to as units of an unsaturated compound (e.g., a "vinyl monomer" or "olefin monomer") to which they are analogous.

Polymers which can be formed from unsaturated monomers such as vinyl monomers and olefin monomers are also referred to by the terms "polyvinyl" and "polyolefin".

Herein, an "unsubstituted" alkylene unit (e.g., ethylene unit) refers to an alkylene unit which does not have any substituent other than the pendant group discussed herein. That is, an alkylene unit attached to the aforementioned pendant group is considered unsubstituted if there are no substituents at any other positions on the alkylene unit.

In some embodiments of any of the respective embodiments described herein, the polymer comprises backbone units (e.g., X in formula I) having formula II (wherein $R_1$-$R_3$ and A are as defined herein):

$$—CR_1R_2—CR_3A- \quad \text{Formula II}$$

When the backbone unit (e.g., X) is not attached to L or Y (i.e., to a pendant group), A is a side chain, such as $R_4$ (as defined herein); and when the backbone unit (e.g., X) is attached to L or Y, A is a covalent bond or a linking group (as defined herein) attaching to L or Y, thus forming a side chain comprising A, L and Y.

When A is a linking group, the linking group may optionally be —O—, —S—, alkylene, arylene, cycloalkyl, heteralicyclic, amine, sulfate, sulfonate, sulfonyl, sulfoxide, phosphate, phosphonyl, phosphinyl, alkoxy, aryloxy, thioalkoxy, thioaryloxy, azo, sulfonamide, carbonyl, thiocarbonyl, carboxy, carbonyl, thiocarbonyl, urea, thiourea, carbamyl, thiocarbamyl, amide, epoxide or amino.

$R_1$-$R_4$ are each independently hydrogen, alkyl, alkenyl, alkynyl, cycloalkyl, aryl, heteroaryl, heteroalicyclic, amine, halide, sulfate, sulfonate, sulfonyl, sulfoxide, phosphate, phosphonyl, phosphinyl, hydroxy, alkoxy, aryloxy, thiohydroxy, thioalkoxy, thioaryloxy, cyano, nitro, azo, azide, sulfonamide, carbonyl, thiocarbonyl, carboxy, thiocarbamate, urea, thiourea, carbamate, amide, epoxide and hydrazine end groups (as defined herein).

Herein, the phrase "linking group" describes a group (e.g., a substituent) that is attached to two or more moieties in the compound.

Herein, the phrase "end group" describes a group (e.g., a substituent) that is attached to a single moiety in the compound via one atom thereof.

When each of $R_1$-$R_3$ is hydrogen, and A is a covalent bond or linking group, the backbone unit (e.g., X) is an unsubstituted ethylene unit attached (via A) to a pendant group described herein.

When each of $R_1$-$R_4$ is hydrogen (and A is $R_4$), the backbone unit (e.g., X) is an unsubstituted ethylene unit which is not attached to a pendant group described herein.

In some embodiments of any of the embodiments described herein, $R_1$ and $R_2$ are each hydrogen. Such embodiments include polymeric backbones formed from many widely used vinyl monomers (including ethylene), including, for example, olefins (e.g., ethylene, propylene, 1-butylene, isobutylene, 4-methyl-1-pentene), vinyl chloride, styrene, vinyl acetate, acrylonitrile, acrylate and derivatives thereof (e.g., acrylate esters, acrylamides), and methacrylate and derivatives thereof (e.g., methacrylate esters, methacrylamides).

In some embodiments of any of the embodiments described herein, $R_3$ is hydrogen. In some such embodiments, $R_1$ and $R_2$ are each hydrogen.

In some embodiments of any of the embodiments described herein, $R_3$ is methyl. In some such embodiments, $R_1$ and $R_2$ are each hydrogen. In some such embodiments, the backbone unit is a unit of methacrylate or a derivative thereof (e.g., methacrylate ester, methacrylamide).

In some embodiments of any of the embodiments described herein relating to formula II, the linking group represented by the variable A is —O, amine, —C(═O)O—, —C(═O)NH— or phenylene. In exemplary embodiments, A is —O—.

For example, the backbone unit may optionally be a vinyl alcohol derivative (e.g., an ester or ether of a vinyl alcohol unit) when A is —O—; a vinylamine derivative (e.g., an amide or substituted amine of a vinylamine unit) when A is —O— an acrylate or methacrylate derivative (e.g., an ester of an acrylate or methacrylate unit) when A is —C(═O)O—; an acrylamide or methacrylamide unit when A is —C(═O)NH—; and/or a styrene derivative (e.g., a substituted styrene unit) when A is phenylene.

A backbone unit substituted by a pendant group described herein (according to any of the respective embodiments)—e.g., X attached to L-Y in formula I—may be the same as or different than the backbone unit which is not substituted by the pendant group (e.g., X which is not attached to L-Y in formula I, when m is at least 1).

In addition, the plurality of backbone units substituted by a pendant group (according to any of the respective embodiments)—e.g., X attached to L-Y in formula I—may be the same as each other or different from each other.

In addition, the plurality of pendant groups attached to a plurality of backbone units—e.g., L-Y in formula I—may be the same as each other or different from each other (e.g., may differ in the identity of L and/or Y.

In addition, the plurality of backbone units not substituted by a pendant group (according to any of the respective embodiments)—e.g., X which is not attached to L-Y in formula I—may be the same as each other or different from each other. For example, a copolymer described herein may comprise both unsubstituted vinyl alcohol backbone units and additional unsubstituted backbone units (e.g., vinyl acetate, vinyl chloride, etc.), in addition to monomeric units comprising a cross-linkable functional group (e.g., as a substituted vinyl alcohol unit).

The number of types of monomeric units comprising a cross-linkable functional group, the number of types of monomeric units which do not a cross-linkable functional group (if any such units are present), the number of types of backbone units substituted by a pendant group, and/or the number of types of pendant group in the polymer, may each independently be any number (e.g., 1, 2, 3, 4, 5, 6, 7, 8, 9, 10 or more).

In any of the embodiments described herein wherein the polymer comprises two or more types of monomeric units, any two or more different types of monomeric unit (e.g., a unit comprising a cross-linkable functional group and a unit without a cross-linkable functional group; two different types of unit with a cross-linkable functional group; and/or two different types of unit without a cross-linkable functional group) may be distributed randomly or non-randomly throughout the polymer. When different types of monomeric unit are distributed non-randomly, the copolymer may be one characterized by any non-random distribution, for example, an alternating copolymer, a periodic copolymer, and/or a block copolymer.

Cross-Linkable Group:

The cross-linkable groups according to any of the respective embodiments described herein may be any cross-linkable group known in the art, and may be attached to any suitable polymer (according to any of the embodiments described herein in the section relating to the polymer).

In some embodiments of any of the respective embodiments described herein, the cross-linkable functional groups are capable of cross-linking with each other via polymerization (e.g., wherein curing of the implant comprises effecting polymerization), for example, via free radical polymerization and/or anionic polymerization, and/or cationic polymerization. Polymerization is optionally effected by contact an initiator, and optionally a photoinitiator, which may be activated by illumination (UV and/or visible illumination) or thermal initiator (decomposition can be from ambient temperature to 70 Celsius degrees).

Examples of functional groups cross-linkable via free radical polymerization include, without limitation, acryl ($H_2C$═CH—C(═O)—) and methacryl ($H_2C$═C($CH_3$)—C(═O)—) groups. Cyanoacryl ($H_2C$═C(C≡N)—C(═O)—) is a non-limiting example of a functional group cross-linkable via anionic polymerization.

A wide variety of additional polymerizable functional groups, as well as suitable initiators for each polymerizable functional group, will be known to the skilled person.

Without being bound by any particular theory, it is believed that polymerizable functional groups (e.g., by free radical polymerization) are particularly suitable for cross-linking a substance in vivo, without causing excessive irritation to tissue.

In some embodiments of any of the respective embodiments described herein, at least a portion of the cross-linkable functional groups are comprised by a pendant group attached to the polymer (e.g., a pendant group represented by the variables L and Y in formula I, according to any of the respective embodiments described herein), that is, they form a side chain (wherein the functional group is attached directly to the polymeric backbone) or a portion of a side chain of the polymer (wherein the functional group is attached to the polymeric backbone via one or more linking group, optionally including —O— or —NH—), rather than form the backbone of the polymer. Optionally, the position of a cross-linkable functional group as a pendant group facilitates cross-linking between backbones.

A pendant group (according to any of the respective embodiments described herein) may optionally be attached directly to the polymeric backbone or to a linking group comprised by a backbone unit in the polymer (according to any of the respective embodiments described herein), for example, a linking group represented by A in formula II, according to any to the respective embodiments described herein.

A functional group (according to any of the respective embodiments described herein) may optionally be attached directly to the polymer (e.g., to the polymeric backbone or to a linking group comprised by a backbone unit). Alternatively or additionally, the functional group (according to any of the respective embodiments described herein) is optionally attached to the polymer via a linking moiety, for example, wherein a pendant group comprises the functional group (e.g., Y in formula I) and the linking moiety (e.g., L in formula I), according to any of the respective embodiments described herein. The linking moiety may optionally be attached directly to the polymeric backbone or to a linking group comprised by a backbone unit in the polymer (according to any of the respective embodiments described herein), for example, a linking group represented by A in formula II, according to any to the respective embodiments described herein.

The linking moiety is optionally selected to facilitate attachment of the functional group to the polymer.

Examples of suitable linking moieties include, without limitation, $—CH_2—CH(OH)—CH_2—O—$, $—CH_2—CH(OH)—CH_2—NR_5—$, $—C(═O)—NH—B—O—$, and $—C(═O)—NH—B—NR_6—$, wherein B is a substituted or unsubstituted alkylene, and $R_5$ and $R_6$ are each independently selected from the group consisting of hydrogen, alkyl, cycloalkyl, heteroalicyclic, aryl, and heteroaryl.

For example, $—CH_2—CH(OH)—CH_2—O—$ and/or $—CH_2—CH(OH)—CH_2—NR_5—$ are optionally obtained by attaching the functional group or polymer to glycidol (e.g., via an ester, ether, amine or amide linking group), and then attaching the polymer or functional group (respectively) to the epoxide group of glycidol (e.g., via attack by a nucleophilic group, such as hydroxy or amine).

In addition, $—C(═O)—NH—B—O—$, and $—C(═O)—NH—B—NR_6—$ are optionally obtained by attaching the functional group or polymer to a compound comprising an isocyanate group (e.g., via an ester, ether, amine or amide linking group)—for example, a compound having the formula $O═C═N—B—OH$ or $O═C═N—B—NHR_6—$ and then attaching the polymer or functional group (respectively) to the isocyanate (e.g., by attack a nucleophilic group, such as hydroxy or amine).

The nature of the second cross-links formed upon cross-linking of the cross-linkable functional groups (e.g., upon curing of the implant) will be understood by the skilled person, in view of any given cross-functional group and in some cases, considering the type of polymer or additional agent present upon cross-linking.

For example, polymerizable functional groups (e.g., acryl, methacryl, cyanoacryl and vinylsulfonyl) will generally form dimeric, trimeric, oligomeric and/or polymeric moieties formed upon polymerization of the polymerizable functional group.

Distribution and Mass of Side Chains and Cross-Links:

As described herein, the properties of the polymer may optionally be controlled by selecting suitable side chains, functional groups (according to any of the respective embodiments described herein) and/or suitable proportions thereof.

Without being bound by any particular theory, it is believed that a low proportion of side chains (due to small size of individual side chains and/or to low molar concentration of side chains) facilitates flexibility in the uncured implant by allowing considerable movement of polymeric backbones relative to one another.

It is to be appreciated that a low average molecular weight (e.g., according to any of the respective embodiments described herein) may optionally be affected both by low molecular weight of individual side chains (e.g., 17 Da for hydroxyl groups in PVA) as well as by a low proportion of side chains with a higher molecular weight (e.g., functional groups capable of cross-linking with each other, which are optionally large, yet present in only a minority of side chains in the polymer).

It is to be appreciated that a weight ratio of side chains to backbone (e.g., according to any of the respective embodiments described herein) may optionally be affected both by an average molecular weight of individual side chains (e.g., according to any of the respective embodiments described herein) as well as by a proportion of side chains, for example, whether the polymer comprises one side chain per monomeric unit (e.g., as in monosubstituted vinyl residues such as vinyl alcohol, vinylamine, vinyl acetate and vinyl chloride residues) or multiple side chains per monomeric unit (e.g., as in tetrafluoroethylene or vinylidene difluoride residues).

In some embodiments of any of the respective embodiments described herein, the polymer comprises more cross-linkable functional groups than monomeric units, that is, few functional groups are bond one to each other in a short side chain.

In some embodiments of any of the respective embodiments described herein, the polymer comprises less cross-linkable functional groups than monomeric units, that is, only a portion of the monomeric units of the polymer comprise a cross-linkable functional group. The other monomeric units may optionally lack a side chain (e.g., ethylene residues) or comprise a small side chain (e.g., —OH, $—NH_2$, halo), which is optionally selected for providing a flexible uncured polymer (e.g., as described herein).

Without being bound by any particular theory, it is believed that a presence of cross-linkable functional groups on only a portion of monomeric units in a polymer is associated with increased flexibility, because of either one of the following mechanisms:

a) The cross-linkable functional groups may be sufficiently large to promote rigidity (e.g., by inhibiting backbone movement) if present in excessively large proportions, e.g., if present in each or almost each monomeric unit.
b) Monomeric units comprising cross-linkable functional groups interspersed with other monomeric units in the form of a copolymer (e.g., a random copolymer) may reduce a degree of crystallinity in the polymer (e.g., by reducing repeatability in the polymer sequence), which may be an important cause of rigidity in some polymers, especially polymers with small side chains.

Alternatively or additionally, the proportion of cross-linkable functional groups in the polymer is determined relative to the molecular weight of the polymer (including the functional groups thereof).

Herein, the term "hydrocarbon" describes an organic moiety that includes, as its basic skeleton, a chain of carbon atoms, substituted mainly by hydrogen atoms. The hydrocarbon can be saturated or non-saturated, be comprised of aliphatic, alicyclic or aromatic moieties, and can optionally be substituted by one or more substituents (other than hydrogen). A substituted hydrocarbon may have one or more substituents, whereby each substituent group can independently be, for example, cycloalkyl, alkenyl, alkynyl, aryl, heteroaryl, heteroalicyclic, amine, halide, sulfate, sulfonate, sulfonyl, sulfoxide, phosphate, phosphonyl, phosphinyl, hydroxy, alkoxy, aryloxy, thiohydroxy, thioalkoxy, thioaryloxy, oxo, cyano, nitro, azo, azide, sulfonamide, carbonyl, thiocarbonyl, carboxy, thiocarbamate, urea, thiourea, carbamate, amide, epoxide and hydrazine. The hydrocarbon can be an end group or a linking group, as these terms are defined herein.

Preferably, the hydrocarbon moiety has 1 to 20 carbon atoms. Whenever a numerical range; e.g., "1 to 20", is stated herein, it implies that the group, in this case the alkyl group, may contain 1 carbon atom, 2 carbon atoms, 3 carbon atoms, etc., up to and including 20 carbon atoms.

Herein, the term "alkyl" describes a saturated aliphatic hydrocarbon end group, as defined herein, including straight chain and branched chain groups. Preferably, the alkyl group has 1 to 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or unsubstituted. Substituted alkyl may have one or more substituents, whereby each substituent group can independently be, for example, cycloalkyl, alkenyl, alkynyl, aryl, heteroaryl, heteroalicyclic, amine, halide, sulfate, sulfonate, sulfonyl, sulfoxide, phosphate, phosphonyl, phosphinyl, hydroxy, alkoxy, aryloxy, thiohydroxy, thioalkoxy, thioaryloxy, cyano, nitro, azo, azide, sulfonamide, carbonyl, thiocarbonyl, carboxy, thiocarbamate, urea, thiourea, carbamate, amide, epoxide and hydrazine.

The term "alkylene" describes a saturated or unsaturated aliphatic hydrocarbon linking group, as this term is defined herein, which differs from an alkyl group (when saturated) or an alkenyl or alkynyl group (when unsaturated), as defined herein, only in that alkylene is a linking group rather than an end group.

Herein, the term "alkenyl" describes an unsaturated aliphatic hydrocarbon end group which comprises at least one carbon-carbon double bond, including straight chain and branched chain groups. Preferably, the alkenyl group has 2 to 20 carbon atoms. More preferably, the alkenyl is a medium size alkenyl having 2 to 10 carbon atoms. Most preferably, unless otherwise indicated, the alkenyl is a lower alkenyl having 2 to 4 carbon atoms. The alkenyl group may be substituted or unsubstituted. Substituted alkenyl may have one or more substituents, whereby each substituent group can independently be, for example, cycloalkyl, alkynyl, aryl, heteroaryl, heteroalicyclic, amine, halide, sulfate, sulfonate, sulfonyl, sulfoxide, phosphate, phosphonyl, phosphinyl, hydroxy, alkoxy, aryloxy, thiohydroxy, thioalkoxy, thioaryloxy, cyano, nitro, azo, azide, sulfonamide, carbonyl, thiocarbonyl, carboxy, thiocarbamate, urea, thiourea, carbamate, amide, epoxide and hydrazine.

Herein, the term "alkynyl" describes an unsaturated aliphatic hydrocarbon end group which comprises at least one carbon-carbon triple bond, including straight chain and branched chain groups. Preferably, the alkynyl group has 2 to 20 carbon atoms. More preferably, the alkynyl is a medium size alkynyl having 2 to 10 carbon atoms. Most preferably, unless otherwise indicated, the alkynyl is a lower alkynyl having 2 to 4 carbon atoms. The alkynyl group may be substituted or unsubstituted. Substituted alkynyl may have one or more substituents, whereby each substituent group can independently be, for example, cycloalkyl, alkenyl, aryl, heteroaryl, heteroalicyclic, amine, halide, sulfate, sulfonate, sulfonyl, sulfoxide, phosphate, phosphonyl, phosphinyl, hydroxy, alkoxy, aryloxy, thiohydroxy, thioalkoxy, thioaryloxy, cyano, nitro, azo, azide, sulfonamide, carbonyl, thiocarbonyl, carboxy, thiocarbamate, urea, thiourea, carbamate, amide, epoxide and hydrazine.

The term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or unsubstituted. Substituted cycloalkyl may have one or more substituents, whereby each substituent group can independently be, for example, alkyl, alkenyl, alkynyl, cycloalkyl, aryl, heteroaryl, heteroalicyclic, amine, halide, sulfate, sulfonate, sulfonyl, sulfoxide, phosphate, phosphonyl, phosphinyl, hydroxy, alkoxy, aryloxy, thiohydroxy, thioalkoxy, thioaryloxy, cyano, nitro, azo, azide, sulfonamide, carbonyl, thiocarbonyl, carboxy, thiocarbamate, urea, thiourea, carbamate, amide, epoxide and hydrazine. The cycloalkyl group can be an end group, as this phrase is defined herein, wherein it is attached to a single adjacent atom, or a linking group, as this phrase is defined herein, connecting two or more moieties.

The term "aryl" describes an all-carbon monocyclic or fused-ring polycyclic (i.e., rings which share adjacent pairs of carbon atoms) end group (as this term is defined herein) having a completely conjugated pi-electron system. The aryl group may be substituted or unsubstituted. Substituted aryl may have one or more substituents, whereby each substituent group can independently be, for example, alkyl, alkenyl, alkynyl, cycloalkyl, aryl, heteroaryl, heteroalicyclic, amine, halide, sulfate, sulfonate, sulfonyl, sulfoxide, phosphate, phosphonyl, phosphinyl, hydroxy, alkoxy, aryloxy, thiohydroxy, thioalkoxy, thioaryloxy, cyano, nitro, azo, azide, sulfonamide, carbonyl, thiocarbonyl, carboxy, thiocarbamate, urea, thiourea, carbamate, amide, epoxide and hydrazine. Phenyl and naphthyl are representative aryl end groups.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furan, thiophene, imidazole, oxazole, thiazole, pyrazole, pyridine, pyrimidine, quinoline, isoquinoline and purine. The heteroaryl group may be substituted or unsubstituted. Substituted heteroaryl may have one or more substituents, whereby each substituent group can independently be, for example, alkyl, alkenyl, alkynyl, cycloalkyl, aryl, heteroaryl, heteroalicyclic, amine, halide, sulfate, sulfonate, sulfonyl, sulfoxide, phosphate, phosphonyl, phosphinyl, hydroxy, alkoxy, aryloxy, thiohydroxy, thioalkoxy, thioaryloxy, cyano, nitro, azo, azide, sulfonamide, carbonyl, thiocarbonyl, carboxy, thiocarbamate, urea, thiourea, carbamate, amide, epoxide and hydrazine. The heteroaryl group can be an end group, as this phrase is defined herein, where it is attached to a single adjacent atom, or a linking group, as this phrase is defined herein, connecting two or more moieties. Representative examples are pyridine, pyrrole, oxazole, indole, purine and the like.

The term "arylene" describes a monocyclic or fused-ring polycyclic linking group, as this term is defined herein, and encompasses linking groups which differ from an aryl or heteroaryl group, as these groups are defined herein, only in that arylene is a linking group rather than an end group.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. Substituted heteroalicyclic may have one or more substituents, whereby each substituent group can independently be, for example, alkyl, alkenyl, alkynyl, cycloalkyl, aryl, heteroaryl, heteroalicyclic, amine, halide, sulfate, sulfonate, sulfonyl, sulfoxide, phosphate, phosphonyl, phosphinyl, hydroxy, alkoxy, aryloxy, thiohydroxy, thioalkoxy, thioaryloxy, cyano, nitro, azo, azide, sulfonamide, carbonyl, thiocarbonyl, carboxy, thiocarbamate, urea, thiourea, carbamate, amide, epoxide and hydrazine. The heteroalicyclic group can be an end group, as this phrase is defined herein, where it is attached to a single adjacent atom, or a linking group, as this phrase is defined herein, connecting two or more moieties. Representative examples are piperidine, piperazine, tetrahydrofuran, tetrahydropyran, morpholine and the like.

As used herein, the terms "amine" and "amino" describe both a —NRxRy end group and a —NRx- linking group, wherein Rx and Ry are each independently hydrogen, alkyl, cycloalkyl, aryl, heteroaryl or heteroalicyclic, as these terms are defined herein. When Rx or Ry is heteroaryl or heteroalicyclic, the amine nitrogen atom is bound to a carbon atom of the heteroaryl or heteroalicyclic ring. A carbon atom attached to the nitrogen atom of an amine is not substituted by =O or =S, and in some embodiments, is not substituted by any heteroatom.

The amine group can therefore be a primary amine, where both Rx and Ry are hydrogen, a secondary amine, where Rx is hydrogen and Ry is alkyl, cycloalkyl, aryl, heteroaryl or heteroalicyclic, or a tertiary amine, where each of Rx and Ry is independently alkyl, cycloalkyl, aryl, heteroaryl or heteroalicyclic.

The terms "hydroxy" and "hydroxyl" describe a —OH group.

The term "alkoxy" describes both an —O-alkyl and an —O-cycloalkyl end group, or —O-alkylene or —O-cycloalkyl linking group, as defined herein.

The term "aryloxy" describes both an —O-aryl and an —O-heteroaryl end group, or an —O-arylene-linking group, as defined herein.

The term "thiohydroxy" describes a —SH group.

The term "thioalkoxy" describes both an —S-alkyl and an —S-cycloalkyl end group, or —S-alkylene or —S-cycloalkyl linking group, as defined herein.

The term "thioaryloxy" describes both an —S-aryl and an —S-heteroaryl end group, or an —S-arylene-linking group, as defined herein.

The terms "cyano" and "nitrile" describe a —C≡N group.

The term "nitro" describes an $—NO_2$ group.

The term "oxo" describes a =O group.

The term "azide" describes an $—N{=}N^{+}{=}N^{-}$ group.

The term "azo" describes an —N=N—Rx end group or —N=N— linking group, with Rx as defined herein.

The terms "halide" and "halo" refer to fluorine, chlorine, bromine or iodine.

The term "phosphate" refers to a —O—P(=O)(ORx)-$OR_Y$ end group, or to a —O—P(=O)(ORx)-O-linking group, where Rx and $R_Y$ are as defined herein, except when referring to a phosphate ion salt such as a calcium phosphate.

The terms "phosphonyl" and "phosphonate" refer to an —P(=O)(ORx)-$OR_Y$ end group, or to a —P(=O)(ORx)-O— linking group, where Rx and $R_Y$ are as defined herein. The term "phosphinyl" refers to a —PRx$R_Y$ group, where Rx and $R_Y$ are as defined hereinabove.

The term "sulfoxide" or "sulfinyl" describes a —S(=O)—Rx end group or —S(=O)— linking group, where Rx is as defined herein.

The term "sulfonyl" describe a $—S(=O)_2$-Rx end group or $—S(=O)_2—$ linking group, where Rx is as defined herein.

The term "sulfonate" describes a $—S(=O)_2—O—$Rx or $—O—S(=O)_2—$Rx end group or $—S(=O)_2—O—$ linking group, where Rx is as defined herein.

The term "sulfate" describes a $—O—S(=O)_2—O—$Rx end group or $—O—S(=O)_2—O—$ linking group, where Rx is as defined herein.

The terms "sulfonamide" and "sulfonamido", as used herein, encompass both S-sulfonamide and N-sulfonamide end groups, and a $—S(=O)_2—$NRx- linking group.

The term "S-sulfonamide" describes a $—S(=O)_2—$NRx$R_Y$ end group, with Rx and $R_Y$ as defined herein.

The term "N-sulfonamide" describes an $RxS(=O)_2—$N$R_Y$— end group, where Rx and $R_Y$ are as defined herein.

The term "carbonyl" as used herein, describes a —C(=O)—Rx end group or —C(=O)— linking group, with Rx as defined herein. The term "aldehyde" herein describes a —C(=O)H end group.

The term "thiocarbonyl" as used herein, describes a —C(=S)—Rx end group or —C(=S)— linking group, with Rx as defined herein.

The terms "carboxy" and "carboxyl", as used herein, encompasses both C-carboxy and O-carboxy end groups, and a —C(=O)—O— linking group.

The term "C-carboxy" describes a —C(=O)—ORx end group, where Rx is as defined herein.

The term "carboxylic acid" describes a —C(=O)—OH end group, or a deprotonated form ($—CO_2^-$) or salt thereof.

The term "I-carboxy" describes a —OC(=O)—Rx end group, where Rx is as defined herein.

The term "urea" describes a —NRxC(=O)—NRyRw end group or —NRxC(=O)—NRy- linking group, where Rx and Ry are as defined herein and Rw is as defined herein for Rx and Ry.

The term "thiourea" describes a —NRx-C(=S)—NRyRw end group or a —NRx-C(=S)—NRy- linking group, with Rx, Ry and Ry as defined herein.

The terms "amide" and "amido", as used herein, encompasses both C-amide and N-amide end groups, and a —C(=O)—NRx- linking group.

The term "C-amide" describes a —C(=O)—NRxRy end group, where Rx and Ry are as defined herein.

The term "N-amide" describes a RxC(=O)—NRy- end group, where Rx and Ry are as defined herein.

The term "carbamyl" or "carbamate", as used herein, encompasses N-carbamate and O-carbamate end groups, and a —OC(=O)—NRx- linking group.

The term "N-carbamate" describes a RyOC(=O)—NRx- end group, with Rx and Ry as defined herein.

The term "O-carbamate" describes an —OC(═O)—NRxRy end group, with Rx and Ry as defined herein.

The term "thiocarbamyl" or "thiocarbamate", as used herein, encompasses O-thiocarbamate, S-thiocarbamate and N-thiocarbamate end groups, and a —OC(═S)—NRx- or —SC(═O)—NRx- linking group.

The terms "O-thiocarbamate" and "O-thiocarbamyl" describe a —OC(═S)—NRxRy end group, with Rx and Ry as defined herein.

The terms "S-thiocarbamate" and "S-thiocarbamyl" describe a —SC(═O)—NRxRy end group, with Rx and Ry as defined herein.

The terms "N-thiocarbamate" and "N-thiocarbamyl" describe a RyOC(═S)NRx- or RySC(═O)NRx- end group, with Rx and Ry as defined herein.

The term "hydrazine", as used herein, describes a —NRx-NRyRw end group or —NRx-NRy- linking group, with Rx, Ry, and Rw as defined herein.

The term "isocyanate", as used herein, describes a —N═C═O group.

As used herein, the term "epoxide" describes a

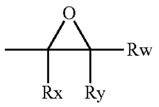

end group or a

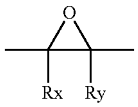

a linking group, as these phrases are defined herein, where Rx, Ry and Rw are as defined herein.

As mentioned above, and related to the cross-linking of the cross-linkable groups, in some embodiments, a slightly cross-linked polymer (also referred to a less-cross-linked configuration) comprises from about 0.1% of cross-links to about 1% of cross-links. Optionally from about 0.05% of cross-links to about 3% of cross-links. Optionally from about 0.01% of cross-links to about 5% of cross-links. In some embodiments, contrary to slightly cross-linked polymer, there is a cross-linked polymer (also referred to a more-cross-linked configuration) which comprises from about 50% of cross-links to about 90% of cross-links. Optionally from about 60% of cross-links to about 95% of cross-links. Optionally from about 70% of cross-links to about 100% of cross-links.

Exemplary Polymer Synthesis

Figure 2:
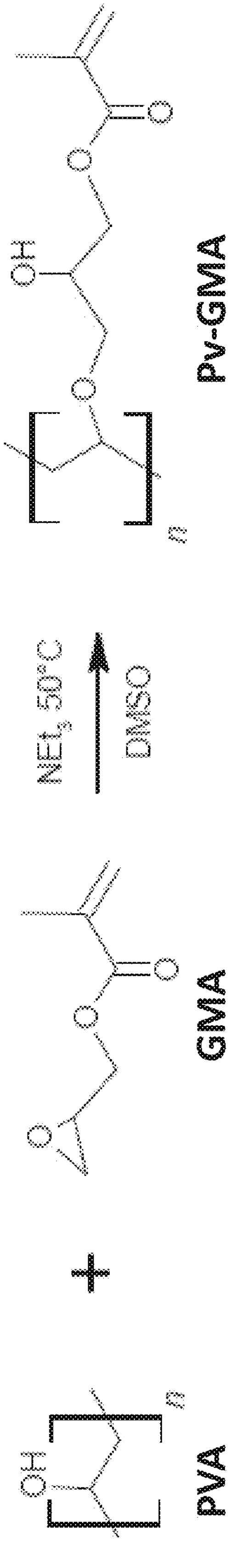
FIG. 2 is a schematic representation of an exemplary polymer synthesis, according to some embodiments of the present invention.

Referring now to FIG. 2, showing a schematic representation of an exemplary polymer synthesis, according to some embodiments, of the present invention. In some embodiments, the synthesis of the exemplary polymers, Pv-GMA, Pv-IMA and Pv-AMA, is performed as follows:

1. Modification Using Glycidyl Methacrylate (Pv-GMA):
   a. 0.5-20 wt % solution of PVA (75-99% hydrolyzed, Mowiol in dry DMSO (USP Standard, Sigma-Aldrich) is heated and evaporated at 95° C. under vacuum.
   b. After cooling to room temperature, GMA (Glycidyl methacrylate, Sigma-Aldrich) and TEA (Triethyl amine, Sigma-Aldrich) are added in molar ratio 3:1 (between 1:1 for low MA concentration to 5:1 for high MA concentration) and 1:50 (between 1:10 for fast reaction to 1:300 for slow reaction) relate to the hydroxyl groups of the PVA respectively. The reaction is carried out at 55° C. (between 48° C. to 65° C.) for 10 hours (2 to 15 hours) under nitrogen.
   c. After cooling to room temperature, the modified polymer is extracted and washed thoroughly few times to clean all left-over monomers, catalysators and solvent (washing solution can be methanol, isopropanol, acetone mixing of them, water or ethers depending on the ratio of MA modification on the polymer).
   d. The final Pv-GMA polymeric product is composed of a plurality of MA unit covalently bounds to carbon chain.

In some embodiments, the average molecular weight of the Pv-GMA polymer is about 130,000 g/mol (can be between 10,000 to 200,000 g/mol).

2. Modification Using 2-isocyanoethyl methacrylate (Pv-IMA):
   a. 0.5-20 wt % solution of PVA (75-99% hydrolyzed, Mowiol) in dry DMSO (USP Standard, Sigma-Aldrich) is heated and evaporated at 95° C. under vacuum.
   b. After cooling to 50° C., dibutyltin dilaurate (DBTDL) and 2-isocyanoethyl methacrylate (IEM) are added in molar ratio of 1:200 (between 1:50-1:300) and 1:1 (between 0.5:1-5:1) relate to the hydroxyl groups of the PVA respectively. The reaction is carried out at 50° C. (between 48° C. to 65° C.) for 12 hours (2 to 15 hours) under nitrogen.
   c. After cooling to room temperature, the modified polymer is extracted and washed thoroughly few times to clean all left-over monomers, catalysators and solvent (washing solution can be methanol, isopropanol, acetone mixing of them, water or ethers depending on the ratio of MA modification on the polymer).
   d. The final Pv-IMA polymeric product is composed of a plurality of MA unit covalently bounds to carbon chain.

In some embodiments, the average molecular weight of the Pv-IMA polymer is about 130,000 g/mol (can be between 10,000 to 200,000 g/mol).

3. Modification Using Methacrylic Anhydride (Pv-AMA):
   a. 0.5-20 wt % solution of PVA (75-99% hydrolyzed, Mowiol) in dry DMSO (USP Standard, Sigma-Aldrich) is heated and evaporated at 95° C. under vacuum.
   b. After cooling to room temperature, TEA (Triethyl amine, Sigma-Aldrich) and methacrylic anhydride (MAH) are added in molar ratio of 1:150 (between 1:50-1:300) and 2:1 (between 0.5:1-5:1) relate to the hydroxyl groups of the PVA respectively. The reaction is carried out at 58° C. (between 48° C. to 65° C.) for 10 hours (2 to 15 hours) under nitrogen.
   c. After cooling to room temperature, the modified polymer is extracted and washed thoroughly few times to clean all left-over monomers, catalysators and solvent (washing solution can be methanol, isopropanol, acetone mixing of them, water or ethers depending on the ratio of MA modification on the polymer).
   d. The final Pv-AMA polymeric product is composed of a plurality of MA unit covalently bounds to carbon chain.

In some embodiments, the average molecular weight of the Pv-AMA polymer is about 130,000 g/mol (can be between 10,000 to 200,000 g/mol).

It should be noted that the names provided to the compounds are exemplary names used to facilitate the reading and comprehension of the invention. It should be clear that other names can be used when other starting materials are used. Therefore, for example, since other materials can be used instead of isocyanoethyl methacrylate, the compounds can be generally called "Pv-EMA" (Pv-ethyl methacrylate), also for example, since other materials can be used instead of anhydride, the compounds can be generally called "Pv-MA" (Pv-methacrylate).

It should be noted, that in every embodiment of the present invention, several washes are performed to secure that no free monomers are left in the final product.

Optional Additions of Additives to the Polymers

In some embodiments, it is desired to have a medical grade implant where the viscosity of the material to be implanted allows an easy delivery into the chosen place, for example, by means of an injector. In some embodiments, plasticizers are added to the polymer to increase the flow and/or thermoplasticity of the polymer by decreasing one or more of: a) the viscosity of the polymer melt; b) the glass transition temperature (Tg); c) the melting temperature (Tm); and d) the elastic modulus of the polymer. In some embodiments, the viscosity (dynamic viscosity) of the material is from about 1000 Pa*s to about 500 Pa*s. Optionally from about 1500 Pa*s to about 300 Pa*s. Optionally from about 2000 Pa*s to about 200 Pa*s. In some embodiments, the plasticizers are internal plasticizers that are added to the polymer (e.g. internal modifications such as etherification or esterification of parts of the hydroxyl groups of the PVA). In some embodiments, the plasticizers are external plasticizers. In some embodiments, external plasticizers are non-covalently bounded molecules added to the polymer. In some embodiments, one or more plasticizers are used. In some embodiments, a mix of plasticizers are used. In some embodiments, a mix of internal plasticizers and external plasticizers are used. In some embodiments, depending on the quantity, a range of products can be achieved from a semi-rigid product to a highly flexible product. In some embodiments, the plasticizer concentration can be between about 1% to about 50% of the final product weight. Optionally between about 5% to about 60% of the final product weight. Optionally between about 0.1% to about 80% of the final product weight. In some embodiments, a preferential concentration of plasticizers is from about 8% to about 12% of the final product weight. In some embodiments, in order to provide a desired elasticity, addition of plasticizer in the abovementioned concentration is performed. In some embodiments, in order to ensure release of internal pressures developing during the polymerization, the elasticity is modified by changing and/or using the concentration of plasticizers as abovementioned. In some embodiments, one or more of the following external plasticizers are used: Citrates molecules (Citric acid ester, Acetyl Tributyl Citrate ATBC, Acetyl (2-ethylhexyl) citrate, or Triethyl citrate) which are known to be non-toxic, Adipates, Trimellitate Anhydride (TMA), Benzoate, and Phthalate plasticizers.

In some embodiments, a required amount of plasticizers is added to the PvGMA in order to reduce the transition glass temperature (Tg) to a desired value, for example to a value between about 5° C. and about 50° C. In some embodiments, a required amount of plasticizer is added to the PvGMA to reduce the elastic modulus of the cured product by a range of from about 0% to about 50%. Optionally by a range of from about 10% to about 60%. Optionally by a range of from about 15% to about 80%.

In some embodiments, a transforming plasticizer is used. In some embodiments, the transforming plasticizer starts as external plasticizer before the curing process and it binds to the polymer during the curing process. In some embodiments, the transforming plasticizer molecule contains an acrylic group that can react with an acrylic group on the polymer. In some embodiments, the transforming plasticizers are based on Acrylic-Citrates, Acrylic-Adipates, or acrylic-PEG.

In some embodiments, a potential advantage of the addition of plasticizers is the reduction of the viscosity of the material to be implanted, which allows an easier implantation when injected into the desired location. In some embodiments, modification of viscosity is a reduction of from about 10% to about 50%. Optionally from about 5% to about 60%. Optionally from about 15% to about 80%. In some embodiments, another potential advantage of the addition of plasticizers is the reduction of the creation of bubbles during the curing process, thereby allowing to achieve a more stable and stronger implant. In some embodiments, in implants without plasticizers, the bubbles generated were found to have a size of about 0.2 mm diameter and in a density of about 12 bubbles/$mm^3$. In some embodiments, in implants with plasticizers, the bubbles generated were found to have a size of about 0.05 mm diameter and in a density of about 3 bubbles/$mm^3$. Optionally, the bubbles generated in presence of plasticizer have a size of about 0.005 mm diameter and in a density of about 1 bubble/$mm^3$. Optionally, the bubbles generated in presence of plasticizer have a size of from about 0.005 mm to about 0.05 mm in diameter and in a density of from about 1 bubble/$mm^3$ to about 5 bubble/$mm^3$.

Another Exemplary Embodiment of an Implant

In some embodiments, the medical implant is configured as a monomers-free methacrylic polymer (also called bone augmentation material in the relevant examples) with three or more phases of solid state. In some embodiments, at the first phase, the polymer is in a reversibly solid state. In some embodiments, during the first phase only the main material is solid, while the activator is kept inert and conserved until reaching the second phase. In some embodiments, at the second phase, the polymer is a flexible and stretchable amorphous semi-liquid. In some embodiments, at the second phase the material is liquid enough to allow injection in the desired location but not liquid enough to leak outside the desired location. In some embodiments, optionally, the polymer can be non or slightly cross-linked during the second phase. In some embodiments, these properties allow the medical implant to be easily inserted through a narrow hole into a cavity and assume the shape of the cavity. In some embodiments, in case that the target place is accessible, for example in open surgery, the medical implant can be directly placed in the target place. In some embodiments, at the third phase, the polymer is irreversibly solid.

In some embodiments, the way to transfer the medical grade implant between the First phase, the Second phase and the Third phase is by changing the temperature of the ambient in which the implant is located. For example, during the First phase, the medical grade implant is kept in the shelf at a temperature below 25° C. In some embodiments, as long as the medical grade implant is kept below 25° C., it will stay reversibly solid while conserving the initiator safe and inert. In some embodiments, in order to transfer the medical grade implant into the Second phase, the temperature is increased to a temperature of from about 25° C. to about 37° C. In some embodiments, as long as the medical grade implant is kept between about 25° C. and about 37° C., it will stay semi-liquid while still keeping the initiator safe and inert. In some embodiments, in order to transfer the medical grade implant into the Third phase, the temperature is increased to a temperature above 37° C. In some embodiments, increasing the temperature above 37° C. will cause the activation of the initiator and therefore of the irreversible polymerization process until the medical grade implant is solid.

As mentioned above, and related to the cross-linking of the cross-linkable groups, in some embodiments, a difference between the phases comprises the transition from a less-cross-linked configuration to a more-cross-linked configuration. In some embodiments, a less-cross-linked configuration comprises from about 0.1% of cross-links to about 1% of cross-links. Optionally from about 0.05% of cross-links to about 3% of cross-links. Optionally from about 0.01% of cross-links to about 5% of cross-links. In some embodiments, a more-cross-linked configuration comprises from about 50% of cross-links to about 90% of cross-links. Optionally from about 60% of cross-links to about 95% of cross-links. Optionally from about 70% of cross-links to about 100% of cross-links.

In some embodiments, the way to achieve this material is by adding glycidyl alkyls (GA) by the same method as disclosed above to decrease the Tg of the polymer and achieve the desired properties of the implant. In some embodiments, the GA can be added to from about 5% to about 90% of the hydroxyl groups of the PVA. In some embodiments, optionally, alkyl ethers are added to the PVA to decrease the Tg of the polymer and achieve the desired properties of the implant. In some embodiments, the GA can be added to from about 5% to about 90% of the hydroxyl groups of the PVA.

Figure 3:
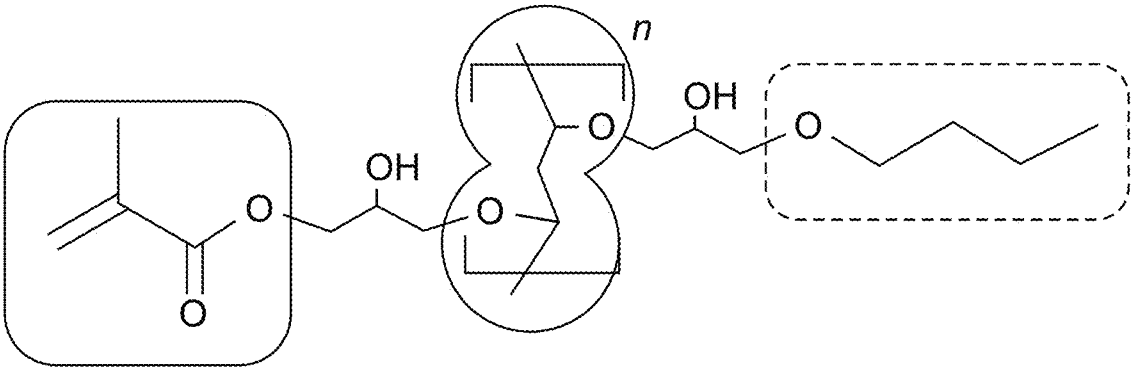
FIG. 3 is a schematic illustration showing a comparison between Pv-GMA-GAE polymer and Pv-GMA-AE, according to some embodiments of the invention.
Figure 3:
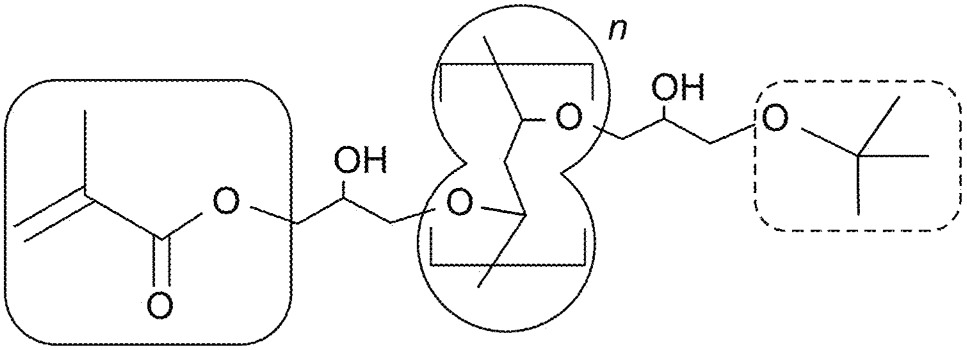
Figure 3:
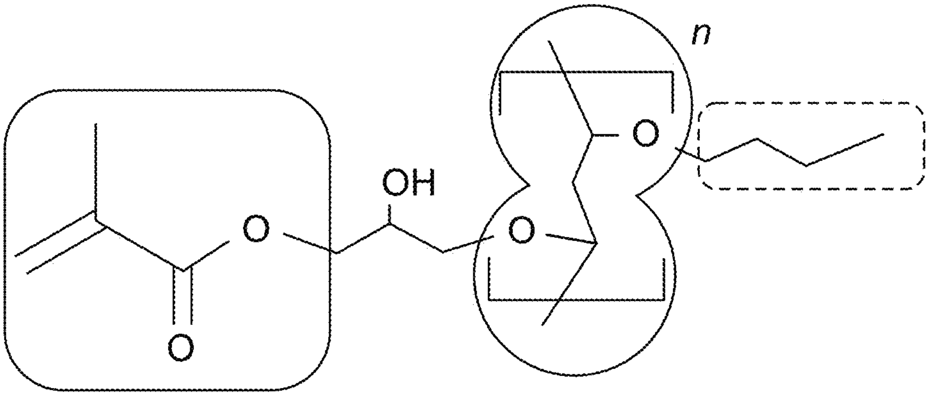

Referring now to FIG. 3, showing a comparison between the Pv-GMA-GAE polymer and Pv-GMA-AE. In some embodiments, the two polymers (PvGMA-AE and PvGMA-GAE) differs from each other mainly by the binding groups of the added molecule (AE-ether, GAE-ester). In some embodiments, the final properties of the polymers highly depend on the composition of the alkyl group of the added molecule, which is almost the same in both. Nevertheless, in some embodiments, the ether bond (in AE) considered as more flexible and stable than the ester bond (in GAE).

In some embodiments, the internal plasticizers can be added by binding glycidyl alkyl ether (GAE) molecules to the polymer hydroxyl group by etherification reaction (see below). In some embodiments, the GAE molecules can be one or more of: Glycidyl ethyl ether, Glycidyl propyl Ether, Glycidyl butyl Ether, Tert-butyl Glycidyl Ether, 2-ethylhexyl glycidyl ether, 2-(2-methoxyethoxy)ethyl glycidyl ether, 2-(2-ethoxyethyl)ethyl glycidyl ether.

In some embodiments, the internal plasticizers are added by binding alkyls molecules to the polymer hydroxyl group by reacting with alkyl halides like: butyl chloride, 1-Chloro-2-methylbutane, 1-Chloro-3-phenylpropane, 1-Bromo-2-methylpropane, 1-Bromobutane, 1-Bromo-3-methylbutane.

In some embodiments, the internal plasticizers are added to from about 1% to about 50% of the polymer units. In some embodiments, the modifications with plasticizer can potentially reduce the polymer transition glass temperature (Tg) to a value between about 5° C. and about 50° C. In some embodiments, the plasticizer can potentially reduce the elastic modulus of the cured product in a range between about 0% to about 50%.

In some embodiments, a potential advantage of using Pv-GMA-GAE polymer and/or Pv-GMA-AE polymer is to provide a polymer that is easy to use and easy to keep in the shelf. In some embodiments, since the material is reversibly solid while keeping the initiator safe and inert, the medical grade implant can be kept indefinitely in the shelf until is needed. In some embodiments, since the material is semi-liquid in the Second phase, it can be easily injected in the desired location.

Modification Using Glycidyl Alkyl Ether (Pv-GAE)

Figure 4A:
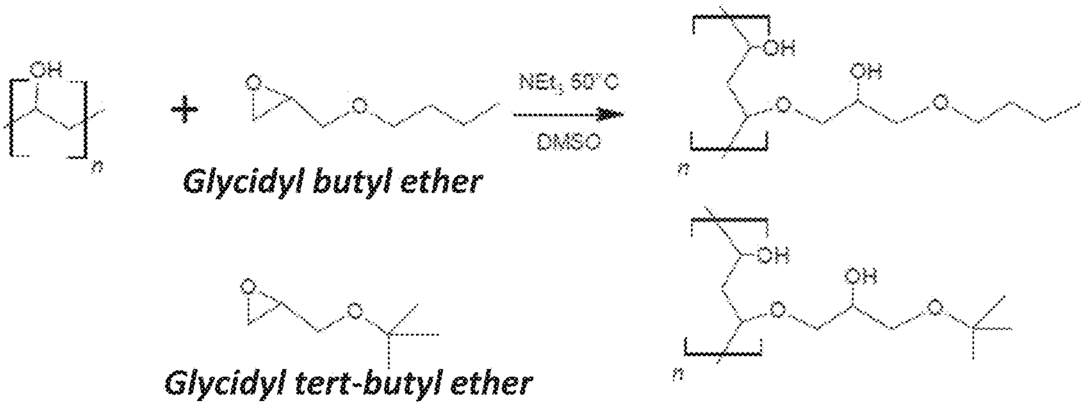
FIGS. 4*a*-4*b* are schematic representations of exemplary polymer modifications, according to some embodiments of the present invention.

Referring now to FIG. 4*a*, showing a schematic representation of a modification using glycidyl Alkyl Ether (Pv-GAE), according to some embodiments of the invention.

a. 0.5-20 wt % solution of PVA (75-99% hydrolyzed, Mowiol) in dry DMSO (USP Standard, Sigma-Aldrich) is heated and evaporated at 95° C. under vacuum.
b. After cooling to room temperature, GAE (Glycidyl Alkyl Ether. e.g.: Glycidyl Butyl Ether, Tert-Butyl Glycidyl Ether, Glycidyl propyl Ether. Sigma-Aldrich) and TEA (Triethyl amine, Sigma-Aldrich) are added in molar ratio 3:1 (between 1:1 for low MA concentration to 5:1 for high MA concentration) and 1:50 (between 1:10 for fast reaction to 1:300 for slow reaction) relate to the hydroxyl groups of the PVA respectively. The reaction is carried out at 55° C. (between 48° C. to 65° C.) for 10 hours (2 to 15 hours) under nitrogen.
c. After cooling to room temperature, the modified polymer is extracted and washed thoroughly few times to clean all left-over monomers, catalysators and solvent (extraction and washing solutions can be tert-Butyl methyl ether, petroleum ether, methanol, isopropanol, acetone, water, ethers or mixing of them depending on the ratio of modification on the polymer).
d. The final Pv-GAE polymeric product is composed of a plurality of alkyl ethers unit covalently bounds to carbon chain.

In some embodiments, the average molecular weight of the Pv-GAE polymer is about 130,000 g/mol (can be between 1,000 to 200,000 g/mol).

In some embodiments, the Pv-GAE is used instead of the PVA for further modification with methacrylic groups in one of the procedures mentioned above.

In some embodiments, the modification reaction with GAE and GMA can be performed together in one reaction. In some embodiments, different ratios of GAE and GMA can be used in order to modify the final properties of the polymer.

Figure 4B:
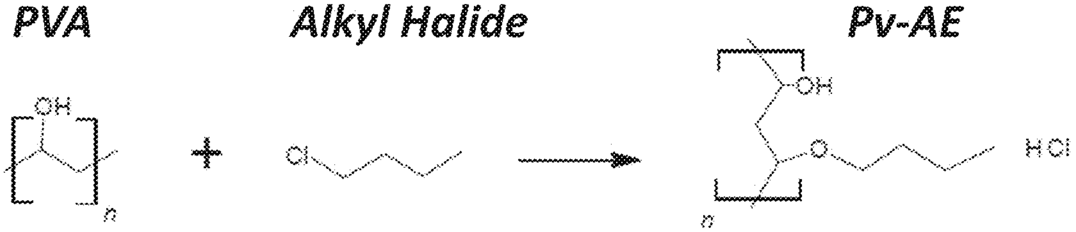

Modification Using Alkyl Halide:

Referring now to FIG. 4*b*, showing a schematic representation of a modification using Alkyl Halide, according to some embodiments of the invention.

a. 0.5-10 wt % solution of PVA (75-99% hydrolyzed, Mowiol) in water was heated to 70° C. for 2 hours for completely dissolving of the polymer.
b. After cooling to room temperature, Alkyl halide (e.g. butyl chloride) was added in a molar ratio of 3:1 (between 0.5 to 5) and a phase-transfer catalyst (e.g. tetrabutylammonium hydrogen sulfate) was added in a ratio of 1:20 (between 1:100 to 1:5) related to the hydroxyl groups of the PVA.
c. The reaction was heated to 75° C. and stirred under reflux for 10 hours.
d. After cooling to R.T. the organic and aqua phases were separated. The modified polymer was extracted and washed thoroughly few times to clean all left-over catalysts and solvent (extraction and washing solutions can be tert-Butyl methyl ether, petroleum ether, methanol, isopropanol, acetone or mixing of them, depending on the ratio of modification on the polymer).

Exemplary Final Product Composition

In some embodiments, the medical implant's bone augmentation material is composed of a solid, yet flexible, Pv-GMA, and, in some embodiments, optionally comprising at least two additives. In some embodiments, the at least two additives are a polymerization initiator and a radiopaque marker. In some embodiments, other additives can be also added, for example, plasticizers, growth factors, pharmaceuticals, chemicals, proteins, and others.

Exemplary Initiator:

In some embodiments, similar to acrylic based materials, the transition from the initial state to the final rigid polymerized state requires addition of suitable polymerization initiators. In some embodiments, initiators can be, for example, the BPO/DMPT (benzoyl peroxide/N,N-dimethyl-p-toluidine) pair for self-curing, the CQ/TA (camphorquinine/tertiary-amine) pair, TPO (diphenyl phosphine oxide) or PPD (phenylpropanedione) for light initiation, or non-toxic derivatives of the AIBN (Azobisisobutyronitrile) molecule which can be initiated by light or by heat (30-80° C.). In some embodiments, the initiators are added to the polymeric bone augmentation material in a molar ratio of 1:250, optionally between 1:50 to 1:500, and relate to the MA groups or 0.01-5% by weight.

In some embodiment, in order to prevent spontaneously activation of the initiator during storage, the polymer was design in a way that its transition glass (Tg) or melting point (Tm) will be between the storage temperature and body temperature. Below the Tg the polymer is in a stiff solid state, eliminating the decomposition of the initiator, while above the Tg the polymer softened therefore enables the initiator decomposition.

In some embodiments, another initiation method is by spatial separation between the initiator and the activator. In some embodiments, the BPO (or other) initiator is homogeneously dispersed in one part of the PvGMA, and the DMPT (or other) activator is homogeneously dispersed in other part of the PvGMA. The two parts are then attached to each other directly or separated by thin pure PvGMA film. In some embodiments, applying force to the matter mixes all parts together, and the mixing of the initiator and activator starts the polymerization reaction and the bone augmentation material transfers into its stiff phase.

In some embodiments, the initiation method is based on spatial separation, both initiator (BPO or other) and activator (DMPT or other) are homogeneously dispersed in the PvGMA, however one of them is capsulated. In some embodiments, applying force to the matter brakes the capsulation and the initiator and activator mixes. In some embodiments, the mixing of the initiator and activator starts the polymerization reaction and the bone augmentation material transfers into its stiff phase.

In some embodiments, the microcapsulation of DMPT (or other) in MA shell can be executed by the following method:

Solution A, containing the capsulated molecules (DMPT, BPO or others), is prepared by mixing the capsulated molecules with MMA (methyl methacrylate), Pv-GMA, or other non-water soluble solvent containing MA (methacrylate) groups in a ratio of 1:1 (between 1:0 to 1:10). Optionally, a small amount of organic soluble photoinitiator can also be added.

Solution B, is prepared by dissolving a water-soluble photoinitiator (For example: the Wako V50 AIBN derivate or others) in water, in a concentration of 0.1-5%. Optionally, a small amount of surfactant can also be added. In some embodiments, the capsulation reaction is executed by spraying solution A into solution B under vigorous mixing. In some embodiments, after receiving uniform distribution of A in B, the mixture is illuminated with the proper UV/Vis light.

In some embodiments, the duration of illumination is from about 10 min to about 1 hour; optionally from about 5 min to about 3 hours; optionally from about 1 min to about 10 hours. In some embodiments, the light source intensity is between 50 $mW/cm^2$ to 2000 $mW/cm^2$. In some embodiments, the mixing rate is from about 100 rpm to about 500 rpm; optionally from about 50 rpm to about 1000 rpm; optionally from about 10 rpm to about 3000 rpm. In some embodiments, the solutions A:B ratio is from about 1:1 to about 1:100 by volume; optionally from about 1:0.5 to about 1:500; optionally from about 1:0.1 to about 1:1000. In some embodiments, the photoinitiator concentration is between 0.05% to 5%. In some embodiments, type of MA molecules can be Pv-GMA, Pv-IMA and Pv-AMA. In some embodiments, the reaction temperature is from about 5° C. to about 70° C.; optionally from about 3° C. to about 90° C.; optionally from about 1° C. to about 150° C. In some embodiments, modification of the abovementioned parameters controls the capsulation size and wall thickness. In some embodiments, the extraction of the capsulations can be achieved by slow centrifugation of the reaction solution, removal of liquids and suspension in methanol/ethanol.

Exemplary Water Sensitive Additives (Method, Amount of Water)

In some embodiments, the trigger for initiation of polymerization (curing) can be exposure to water. In some embodiments, acrylic molecules such as Cyanoacrylates (CAs), which are sensitive to water, spontaneously polymerize when exposed to moisture. In some embodiments, longer-chain CAs, such as n-butyl and 2-octyl 2-cyanoacrylate, are being used as surgical skin and tissue adhesives. In some embodiments, few CAs monomers are mixed with the acrylic polymer (e.g. PvGMA). In some embodiments, as long as the product is in dry storage, no polymerization will occur. In some embodiments, during the procedure, the material is injected and exposed to body liquids and moisture that reacts with the CAs and starts an anionic polymerization reaction. In some embodiments, the CAs molecules are added by 0.1 to 5% of the polymer weight.

In some embodiments, adding certain electron-rich vinyl monomers (e.g. styrene) will initiate a radical polymerization reaction.

Exemplary Radiopaque Markers

In some embodiments, during the injection of the bone augmentation material into the bone, the physician needs to track the bone augmentation material location. Since polymers are transparent to x-ray, the visualization of the bone augmentation material is achieved by adding a radiopaque additive. In some embodiments, radiopaque markers like Barium sulfate, Zirconium dioxide or both are added to the bone augmentation material at a ratio of 10% (between 5-40%) by weight.

Exemplary Preparation of the Final Material

In some embodiments, the Pv-GMA (or Pv-IMA or Pv-AMA) polymer is immersed in organic solvent, for example acetone, methanol, ethanol or isopropanol. In some embodiments, after full immersion, the initiator is added and the solution is filtered, optionally through 0.22-micron filter. In some embodiments, optionally, the required radiopaque material e.g. barium sulfate or zirconium oxide is then added.

In some embodiments, the preparation of the final shaped, amorphous solid material out of the final suspension is as follows:

In some embodiments, the suspension is poured in to a mold. In some embodiments, the mold is then left open until evaporation of the solvent and crystallization of the polymer are achieved, optionally using evaporator.

In some embodiments, the shape of the mold cavity creates the size and shape of the final amorphous solid material. In some embodiments, the amorphous solid material is cut to the final shape and size. In some embodiments, the final shape and size is achieved by combining several pieces of the amorphous solid material.

In some embodiments, the final shaped amorphous material is then loaded into the delivery device.

In some embodiments, the delivery device is used instead of the mold and the suspension is directly poured into the delivery device while evaporating the solvent.

In some embodiments, an anti-solvent extraction method is used in order to extract the polymer. In some embodiments, in this method, the polymer solution is injected into a tank filled with anti-solvent, e.g. water. In some embodiments, the solvent is transferred into the anti-solvent and a solid polymer appears.

Figure 5:
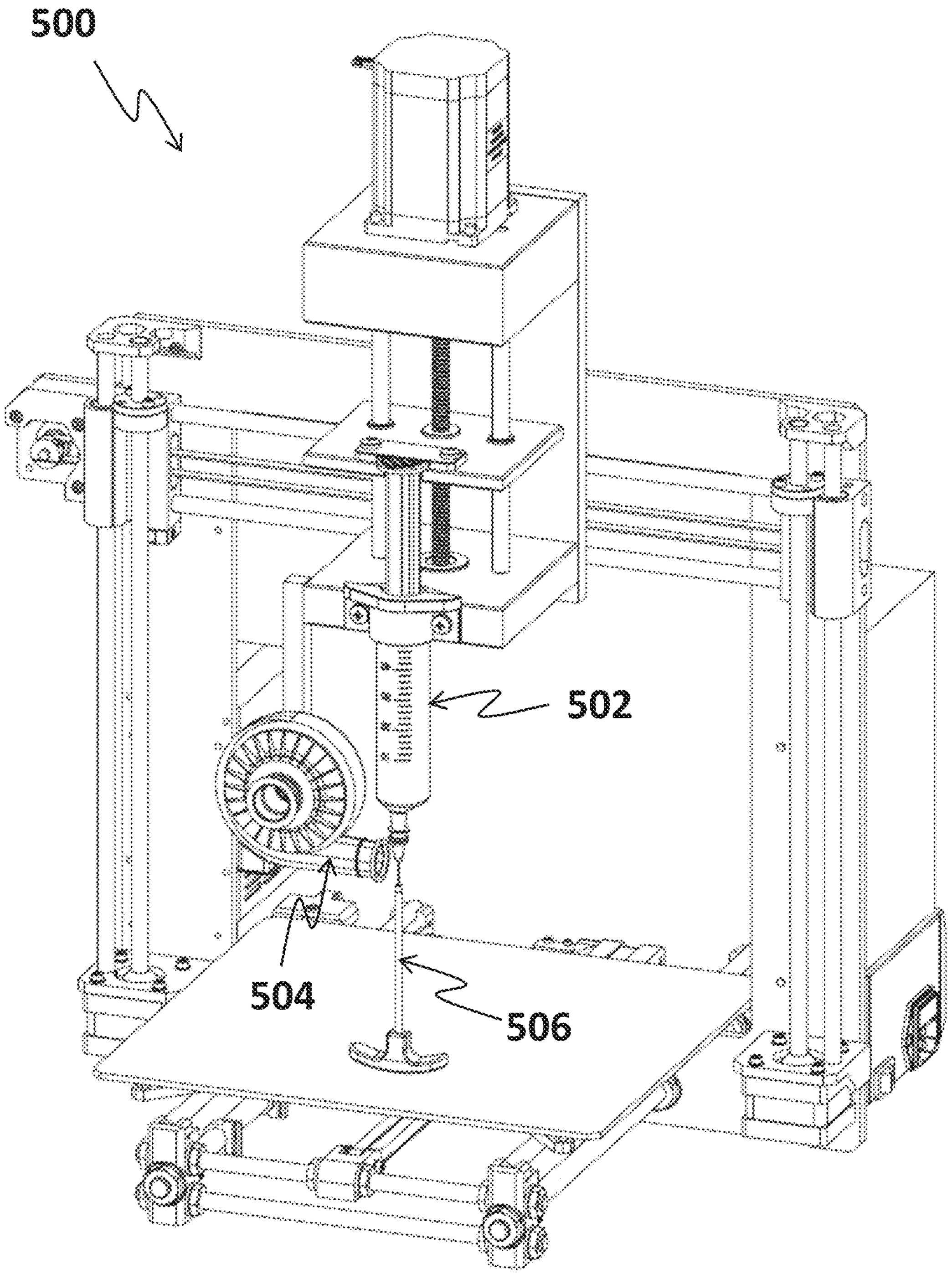
FIG. 5 is a schematic representation of a filling device, according to some embodiments of the present invention.

In some embodiments, the suspension is left over open under stirring, for evaporation of the solvent until receiving high concentrated and viscous suspension. In some embodiments, the well mixed viscous suspension is injected through a syringe 502 and through a drying gas steam 504. In some embodiments, the dry strips are then inserted into an implant or into the delivery device 506, as shown, for example, in FIG. 5, which shows an exemplary embodiment of a filling device 500, according to some embodiments of the present invention. In some embodiments, the aperture in the syringe from which the material exits the syringe can comprise different sizes, shapes and/or cross sections, to enable the material to be formed in different sizes, shapes and/or cross sections.

Exemplary Implant Preparation and Delivery

In some embodiments, the bone augmentation material is casted into molds to form strips shaped with:

- a diameter from about 1 mm to about 10 mm, optionally from about 0.5 mm to about 20 mm, optionally from about 0.1 mm to about 100 mm, for example 0.3 mm, 2 mm, 2.8 mm, 3 mm, 5 mm, 50 mm; optionally bigger or smaller or any number in-between; and
- a length from about 10 mm to about 100 mm, optionally from about 5 mm to about 200 mm, optionally from about 1 mm to about 1000 mm, for example 20 mm, 100 mm, 200 mm, 500 mm, 750 mm; optionally bigger or smaller or any number in-between.

In some embodiments, the molds can have other shapes and/or dimensions.

In some embodiments, a strip of from about 1 cc to about 10 cc, optionally from about 0.5 cc to about 50 cc, optionally from about 0.1 cc to about 100 cc, for example 1.25 cc, 2 cc, 7 cc, 20 cc, 75 cc, optionally bigger or smaller or any number in-between, is entered into the delivery tube. In some embodiments, the final, filled delivery tubes are packed and sterilized. In some embodiments, the production is performed in an aseptic environment, thus no additional sterilization is needed.

Exemplary Embodiments of Delivery Device

Figure 6:
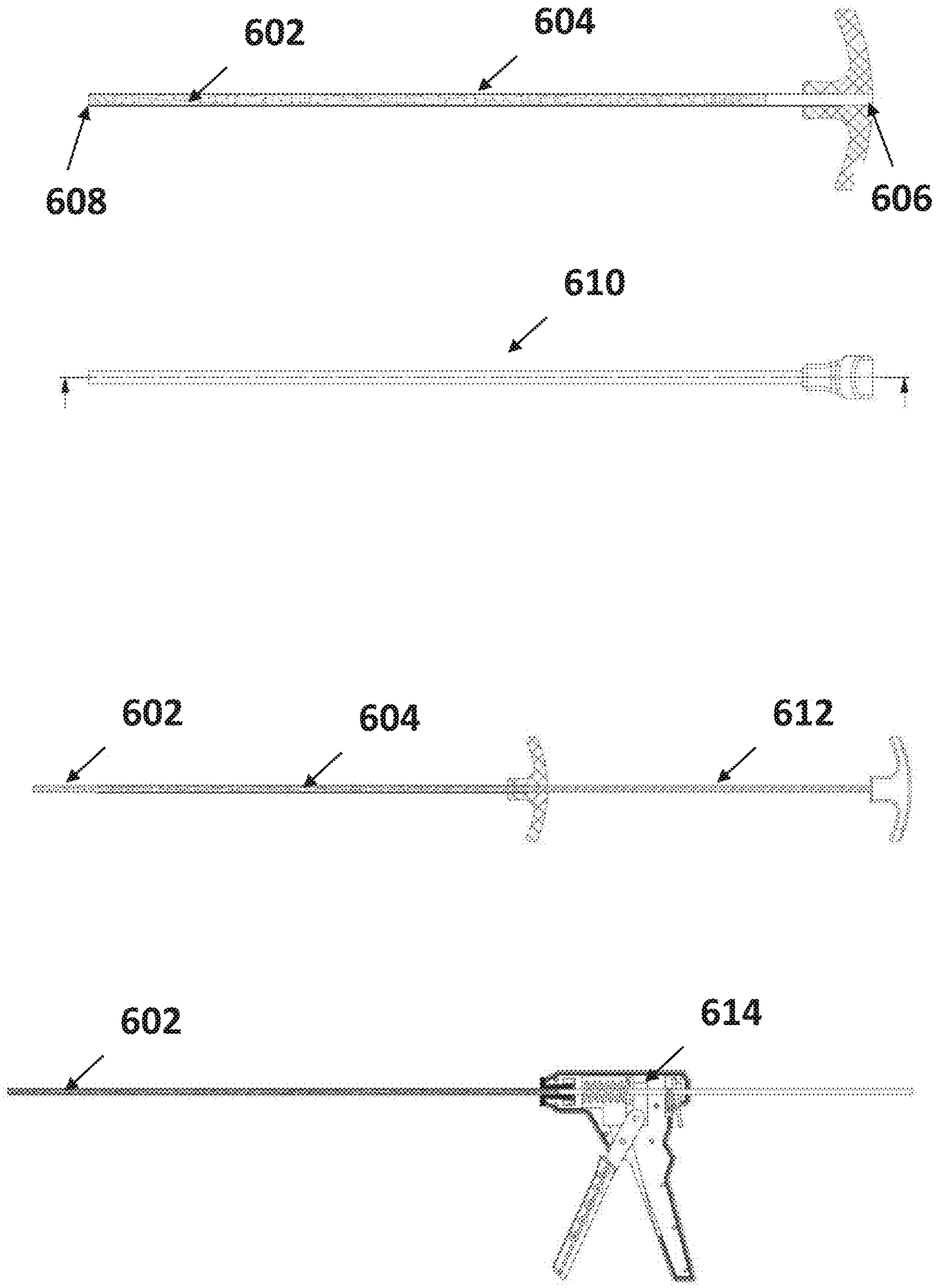
FIG. 6 are schematic representations of exemplary delivery devices, according to some embodiments of the present invention.

Referring now to FIG. 6, showing schematic representations of exemplary delivery devices, according to some embodiments of the present invention. In some embodiments, bone augmentation material 602 is inserted in a tube 604 having 2 openings, proximal opening 606 and distal opening 608. In some embodiments, using a delivery device 610, the distal opening 608 is brought to the site of implantation. In some embodiments, once there, using a plunger-like device 612, the bone augmentation material 602 is released into the desired location. In some embodiments, instead of using a syringe-plunger mechanism, the bone augmentation material 602 is delivered using a mechanical power boost device 614. In some embodiments, other mechanisms can be used, for example, hydraulic mechanisms, electric powered mechanisms and wireless powered mechanisms. In some embodiments, the distal opening 608 comprises a smaller diameter and/or a different shape than the tube 604. In some embodiments, this may be advantageous because the opening 608 acts as a "bottle neck" an allows more control of the deployment of the material in the sense of quantity of material deployed and/or velocity of deployment and/or accuracy of filling of areas due to controlled deployment. In some embodiments, additionally and/or optionally, distal opening 608 may be implemented as a side hole and not necessarily at the tip of the tube 604. In some embodiments, additionally and/or optionally, there are more than one distal opening.

In some embodiments, the delivery device comprises a cutting mechanism adapted to cut and/or stop the delivery of the bone augmentation material into the desired site. In some embodiments, bone augmentation material is delivered inside an implantable device. In some embodiments, once the implantable device is positioned inside the body of the patient, the bone augmentation material is released from inside the implantable device thereby trapping and/or enclosing and/or fixating the implantable device in the location (see Screws internal fixation part below, for examples).

Figure 7A:
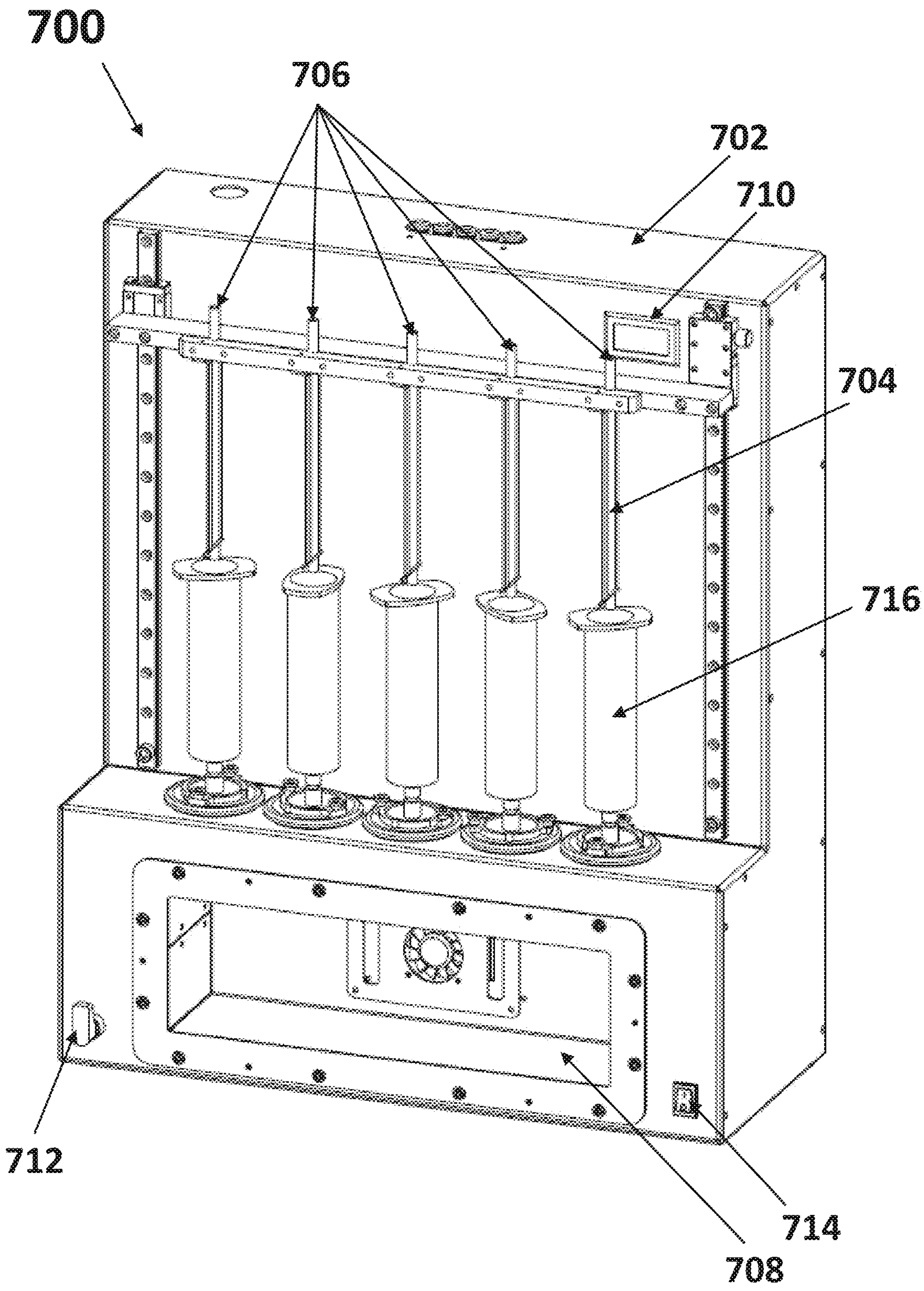
FIG. 7*a* is a schematic representation of an exemplary packaging device, according to some embodiments of the invention.

Referring now to FIG. 7*a*, showing a schematic representation of a packaging device 700, according to some embodiments of the invention. In some embodiments, the packaging device 700 performs a plurality of actions, for example filling cartridges, mixing the material, evaporating the solvent, etc. In some embodiments, the packaging device comprises a main body 702, one or more mixing blades 704, one or more nitrogen inlets 706, one or more temperature-controlled chambers 708, one or more graphical unit interface (GUI) 710, a nitrogen valve 712 and a general on/off switch 714. In some embodiments, the packaging device 700 can fill one or more cartridges and/or syringes 716. In some embodiments, the packaging device 700 is kept in an aseptic environment (for example an ISO5 clean room). In some embodiments, the packaging device 700 is used for the final production stage, as shown for example in FIG. 8.

Figure 7B:
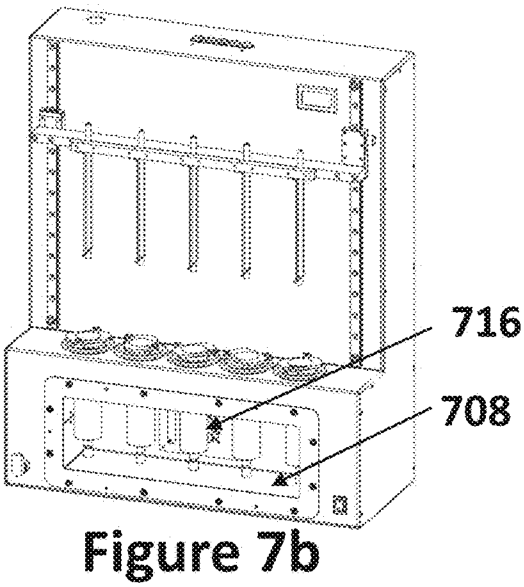
FIGS. 7*b*, 7*c* and 7*d* are schematic representations of the use of the packaging device shown in FIG. 7*a*, according to some embodiments of the invention.
Figure 7C:
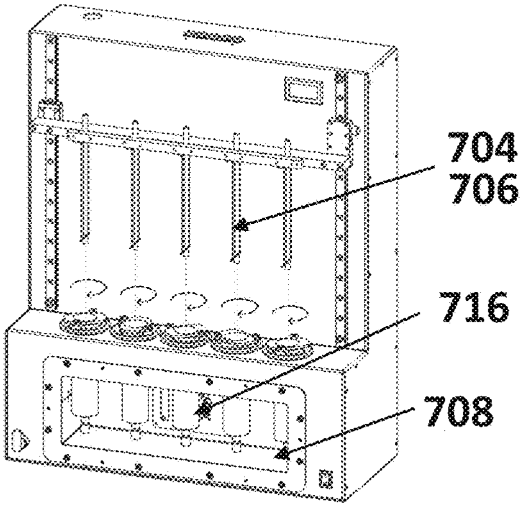
Figure 7D:
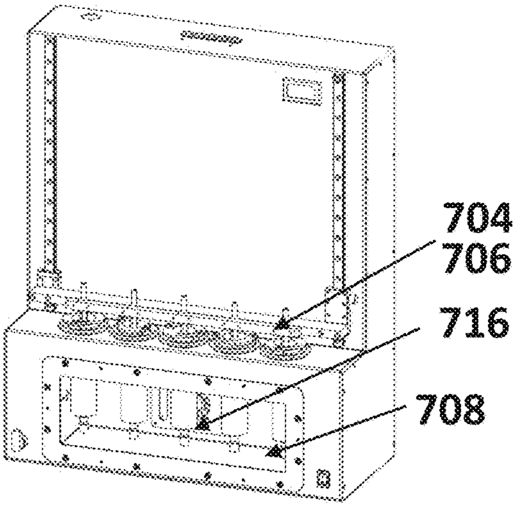

Referring now to FIGS. 7*b-d*, showing schematic illustrations of the use of the packaging device 700, according to some embodiments of the invention. In some embodiments, empty cartridges 716 are loaded into the device so the body of the cartridges are located inside the temperature-controlled chamber 708, as shown for example in FIG. 7*b*. In some embodiments, optionally, the cartridges are the final product storage chamber. In some embodiments, optionally temporary vials (for example a syringe) are used. In some embodiments, when syringes are used, the final cartridges are loaded and filed at a later stage. In FIGS. 7*a-d* are shown five cartridges (or syringes), it should be understood that a smaller or larger number of cartridges/syringes can be filled, according to the capabilities of the packaging device. It should also be understood that a packaging machine adapted to fill, for example, five cartridges at the same time, does not require to have all five cartridges in order to work.

Figure 8:
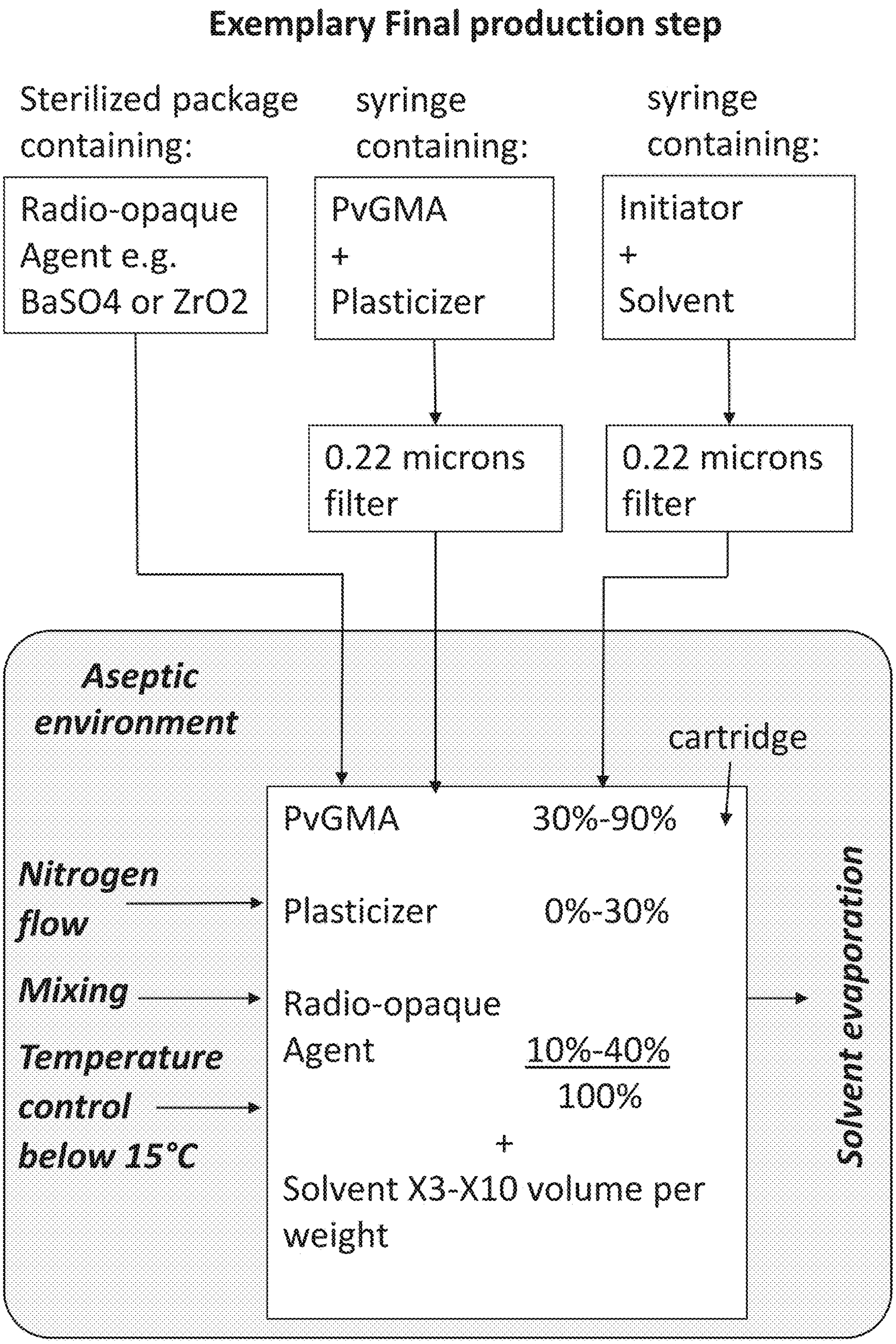
FIG. 8 is a schematic representation of an exemplary final production step, according to some embodiments of the invention.

In some embodiments, the cartridges are then filled with the final ingredients, as described for example in FIG. 8. In some embodiments, each cartridge is filed with ingredients to form, for example, 6 ml of final material (after solvent evaporation). In some embodiments, larger or smaller quantities of material can be inserted in the cartridges, according to the capacities of the cartridges. In some embodiments, optionally, all ingredients are inserted into the cartridge at once. In some embodiments, optionally, ingredients are inserted sequentially during the mixing and evaporation process.

In some embodiments, the cartridges loaded into the packaging device 700 are kept cooled by the temperature-controlled chamber 708. In some embodiments, the temperature inside the temperature-controlled chamber 708 is below the temperature required to activate the initiator (Initiator activation temperature) used in the mix. In some embodiments, the mixing blades 704 and nitrogen inlets 706 are inserted into each cartridge, as shown for example in FIG. 7*d*. In some embodiments, the mixing blades 70 are rotated, while the cartridges 716 are still, as shown for example in FIG. 7*c*. In some embodiments, optionally the mixing blades 704 are still and the cartridges 716 are rotated. In some embodiments, the rotation speed is between about 5 RPM to about 100 RPM. Optionally from about 3 RPM to about 500 RPM. Optionally from about 1 RPM to about 1000 RPM. In some embodiments, during the entire mixing process nitrogen gas is flown from the lower end of the cartridge into the cartridge itself. In some embodiments, the flow rate of the insertion of the nitrogen is of from about 1 liter/min to about 20 liter/min. In some embodiments, optionally, nitrogen is flown during certain points of the mixing process. In some embodiments, a potential advantage of flowing nitrogen during certain points is to decelerate the solvent evaporation process. In some embodiments, the mixing and evaporation process takes between about 10 minutes to 8 hours, depending on the amount of solvent and the nitrogen gas flow. In some embodiments, the mixing and evaporation process ends when all the solvent is evaporated. In some embodiments, optionally, solvent residuals are left in the cartridge. In some embodiments, at this stage, the material in the cartridge is final and ready to be used. In some embodiments, cartridges are then unloaded from the device, sealed and packed. In some embodiments, when temporary vials are used, the final material is then transferred from the vials to the final cartridges.

Referring now to FIG. 8, showing a schematic representation of an exemplary final production step, according to some embodiments of the invention. In some embodiments, as mentioned above, the final production step is performed in the packaging device 700 located in an aseptic environment. In some embodiments, PvGMA together with a plasticizer are passed through a 0.22 microns filter into the cartridge. In some embodiments, an initiator together with a solvent are passed through a 0.22 microns filter into the cartridge. In some embodiments, a radio-opaque agent from a sterilized package is inserted into the cartridge. In some embodiments, different quantities of the PvGMA, plasticizer, initiator, radio-opaque agent and solvent are used to achieve a 100% of material (without the solvent) in between about 3 times to about 10 times of the quantity of material in solvent. For example, in 100 gr of final material, the quantity of solvent used is between about 300 ml and 1000 ml. In some embodiments, as stated above, the mixing is performed in a controlled temperature, for example below 15° C. and while flowing nitrogen into the mix.

Exemplary Curing—From Flexible to Stiff

In some embodiments, the curing process changes the polymer from its initial flexible phase to its final stiff phase. One disadvantage of most prior art cements is that the curing process starts before the injection, therefore the working time until final hardening of the bone augmentation material is limited to about 10 minutes. In some embodiments, in the polymer of the present medical implant, the curing process begins proactively during or after placement, therefore, the working time is not limited.

In some embodiments, the hardening of the polymer during curing is a result of polymerization of the MA groups. In some embodiments, the initiation of the MA polymerization is induced either by free radicals or by anionic initiators or by cationic initiators. In some embodiments, the generation of the free radicals in the bone augmentation material is performed, for example, by either a chemical reaction between peroxides (BPO (Benzoyl peroxide) for example) and activators (DMPT (N,N dimethyl-p-toluidine) for example), or by heat/light (e.g. AIBN (Azobisisobutyronitrile) based molecules). An advantage of the bone augmentation material of the present invention is that the polymerization process starts proactively only after positioning by the use of either heat or light sensitive initiators. In some embodiments, the source of the heat is the natural body heat of the patient, thereby providing an implant that begins polymerization only once positioned in the body of the patient.

In some embodiments, after filling the bone augmentation material into the target site, a suitable initiation probe is inserted to the site. In some embodiments, for example, when using light induced initiators (e.g AIBN based initiator) a light probe (e.g 365 nm, Vis or 250 nm) is inserted to activate the curing process. In some embodiments, the MA groups start to polymerize and cross-links are created between the polymers.

In some embodiments, the time for the curing process with UV is from about 2 seconds to about 3 minutes for 80% of curing. In some embodiments, the time for the curing process with UV is from about 10 seconds to about 2 minutes for 80% of curing. In some embodiments, the time for the curing process with UV is from about 30 seconds to about 1 minutes for 80% of curing. In some embodiments, the time for the curing process with UV is from about 1 second to about 20 minutes for 80% of curing.

In some embodiments, the time for the curing process with UV is from about 1 hour to about 8 hours for 100% of curing. In some embodiments, the time for the curing process with UV is from about 2 hour to about 6 hours for 100% of curing. In some embodiments, the time for the curing process with UV is from about 3 hour to about 4 hours for 100% of curing. In some embodiments, the time for the curing process with UV is from about 1 hour to about 24 hours for 100% of curing. In some embodiments, the time for the curing process with UV is from about 1 hour to about 48 hours for 100% of curing.

In some embodiments, the curing of the delivered implant is performed by exposing the implant to specific temperatures. In some embodiments, a thermal initiator (e.g. 2,2'-Azobis(4-methoxy-2,4-dimethylvaleronitrile) above 30° C., 2,2'-Azobis(2,4-dimethylvaleronitrile) above 45° C., Dimethyl 2,2'-azobis(2-methylpropionate)) above 60, 2,2'-Azobis(2-methylpropionamidine)dihydrochloride above 55, 2,2'-Azobis[2-(2-imidazolin-2-yl)propane]dihydrochloride above 42° C., for example, is added to the polymer.

In some embodiments, exposing the polymer to temperature of about 30 degrees Celsius to about 60 degrees Celsius cures the polymer. In some embodiments, the curing temperature is in the rage of about 45 degrees Celsius to about 55 degrees Celsius. In some embodiments, the body temperature is high enough for the curing process. In this case, there is no need to apply any external heating source.

In some embodiments, the heating will produce free radicals in the polymer. In some embodiments, the radicals would start a chain reaction between the methacrylic groups to form crosslinking network. In some embodiments, the heating of the implant can be achieved by inserting heating probe to the implantation site.

In some embodiments, the time for the curing process with heat is from about 2 minutes to about 30 minutes for 80% of curing. In some embodiments, the time for the curing process with heat is from about 5 minutes to about 20 minutes for 80% of curing. In some embodiments, the time for the curing process with heat is from about 7 minutes to about 10 minutes for 80% of curing.

In some embodiments, the time for the curing process with heat is from about 1 hour to about 8 hours for 100% of curing. In some embodiments, the time for the curing process with heat is from about 2 hour to about 6 hours for 100% of curing. In some embodiments, the time for the curing process with heat is from about 3 hour to about 4 hours for 100% of curing. In some embodiments, were curing is done by the body temperature, reaching 100% curing may take several hours or several days.

Exemplary Mechanical Characteristics

In some embodiments, the implant in its soft configuration comprises the following characteristics:

Density

In some embodiments, the density ($g/cm^3$): is from about 0.05 $g/cm^3$ to about 4 $g/cm^3$. In some embodiments, the density ($g/cm^3$): is from about 0.1 $g/cm^3$ to about 3 $g/cm^3$. In some embodiments, the density ($g/cm^3$): is from about 0.8 $g/cm^3$ to about 2 $g/cm^3$.

Elastic Modulus

In some embodiments, the elastic modulus (MPa): is from about 0.001 MPa to about 1 MPa. In some embodiments, the elastic modulus (MPa): is from about 0.01 MPa to about 0.1 MPa. In some embodiments, the elastic modulus (MPa): is from about 0.05 MPa to about 0.1 MPa. In some embodiments, the elastic modulus is selected according to the specific site to which will be implanted. In some embodiments, at high density, the implant is characterized by a higher modulus of elasticity and vice versa. In some embodiments, the implant is produced by layers instead of one bulk. This will enable controlling the direction of elasticity so that the final hardened implant will have higher elasticity in one direction and lower in another.

In some embodiments, the implant in its hard (or stiff) configuration comprises the following characteristics:

Elastic Modulus

In some embodiments, the elastic modulus (MPa): is from about 1 MPa to about 500 MPa. In some embodiments, the elastic modulus (MPa): is from about 2 MPa to about 150 MPa. In some embodiments, the elastic modulus (MPa): is from about 5 MPa to about 100 MPa.

In some embodiments, the uncured material is an amorphous solid comprising high elasticity. In some embodiments, two pieces of uncured material can be united by applying force towards each other.

In some embodiments, the cured material loses its elasticity, it keeps the form that it had during the curing process and two cured pieces cannot be united by applying pressure towards each other.

Exemplary Procedures

In some embodiments, non-cross-linked or slightly cross-linked bone augmentation material comprising at least one initiator is delivered into the required place. In some embodiments, cross-linking of the polymers in the bone augmentation material begins only at the location due to exposure to stimuli, in this case, for example, the natural body heat of the patient (see above definition of slightly cross-linked/less-cross-linked and more-cross-linked).

Exemplary Experimental Procedure on Cadavers

Experiment on a cadaver: Injection of bone augmentation material into vertebrae.

Figure 9:
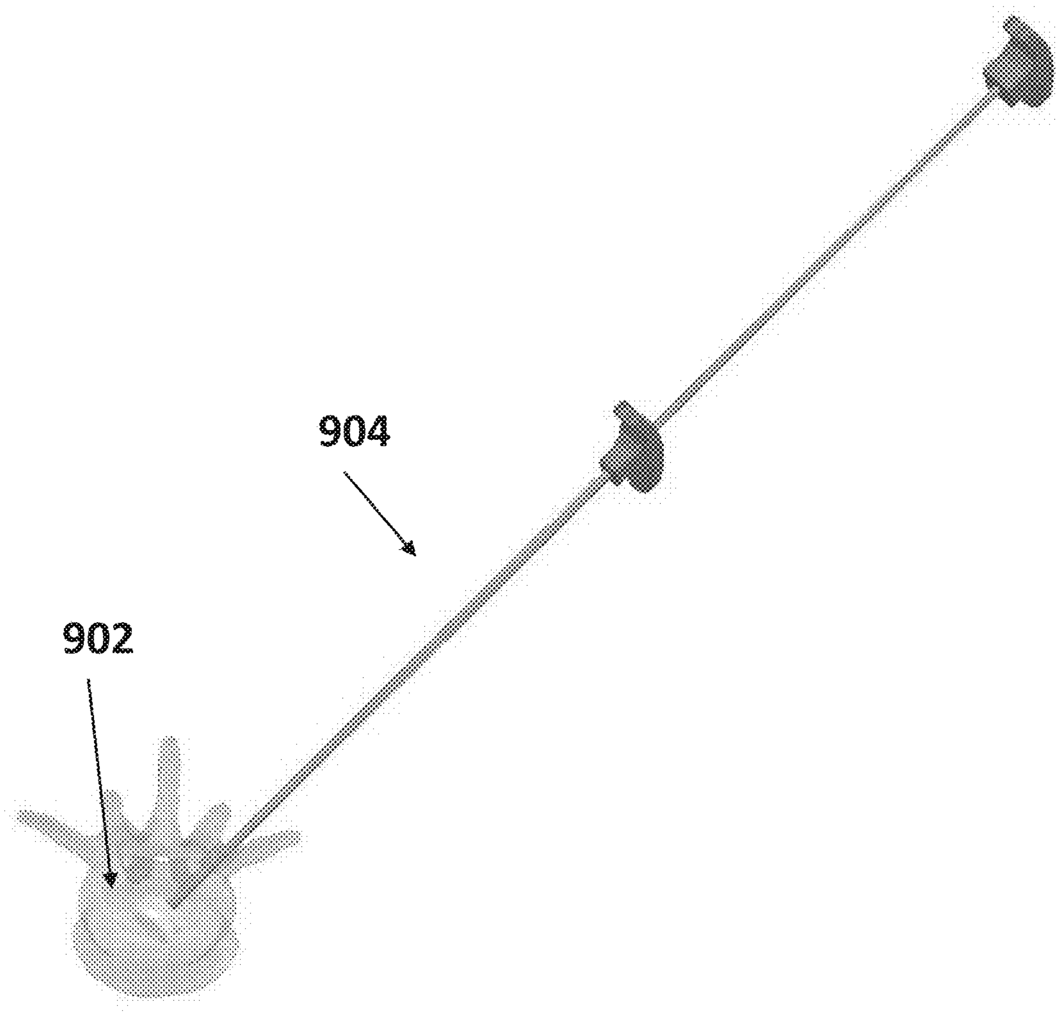
FIG. 9 is a schematic representation of injection of bone augmentation material in a vertebra, according to some embodiments of the present invention.

Experiment Details 8.2 grams of bone augmentation material was injected in T11 vertebra 902 of a 82 years old female by bilateral Kyphoplasty, as schematically shown in FIG. 9, using a plunger type device 904, as previously explained.

Experiment Results

Referring now to FIGS. 10*a-d* showing images of the results of the experiment.

Figure 10A:
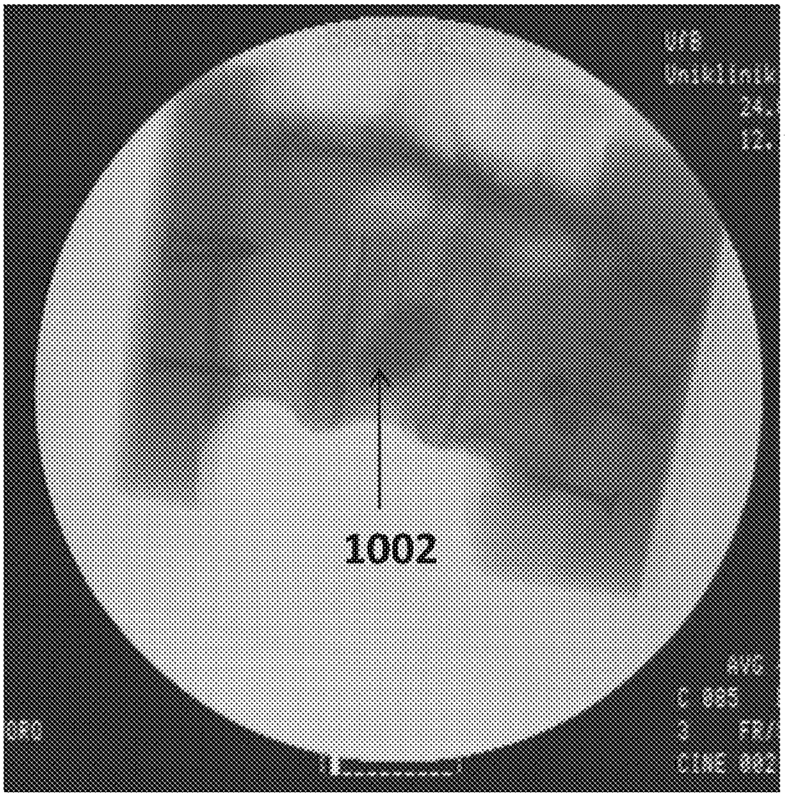
FIGS. 10*a*, 10*b*, 10*c* and 10*d* are images of the results of an experiment performed on a cadaver.
Figure 10B:
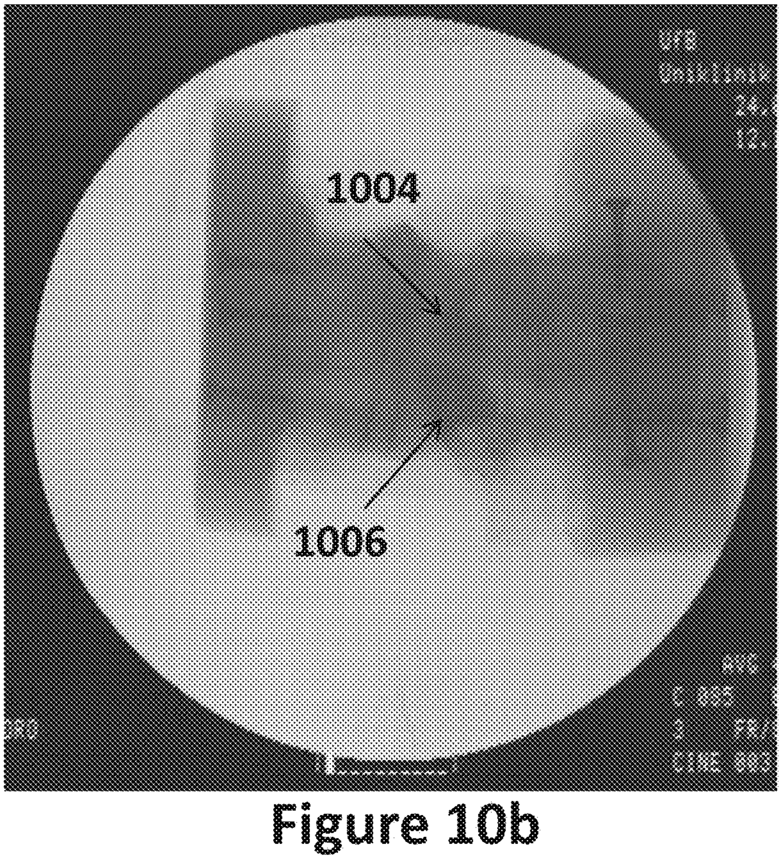
Figure 10C:
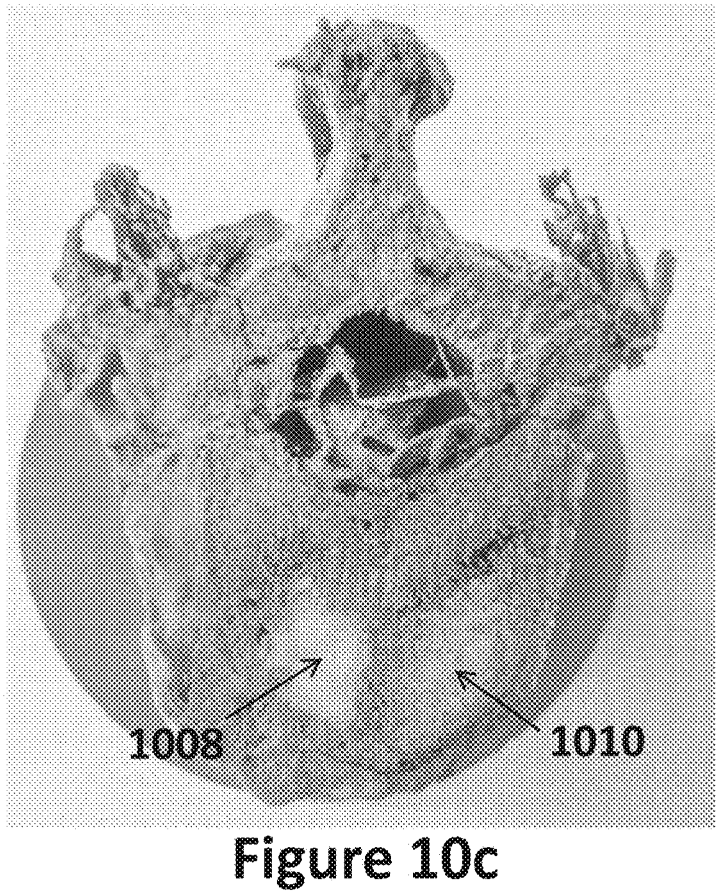
Figure 10D:
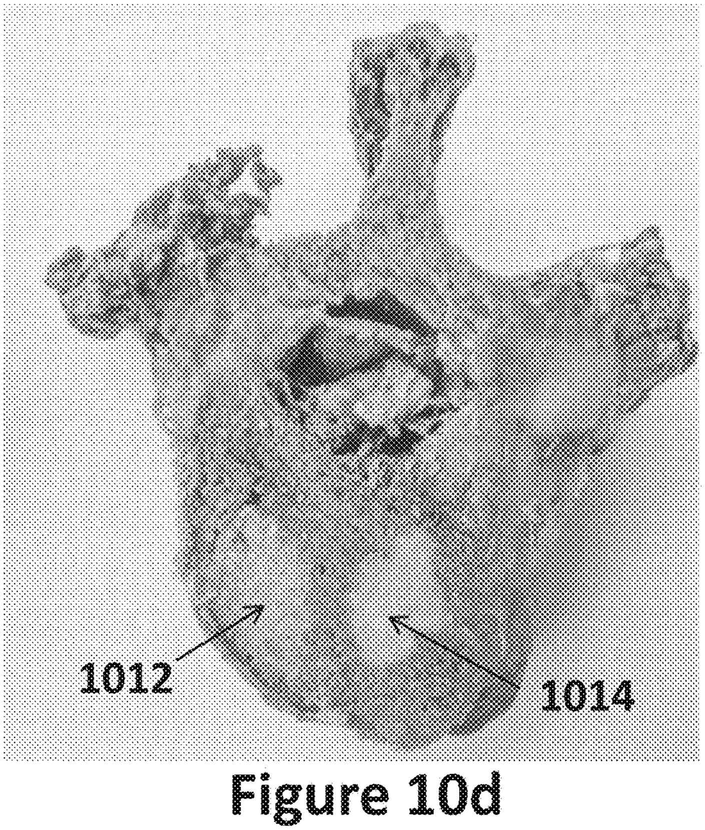

FIG. 10*a* shows a Lateral X-ray image of the T11 vertebra filled with the bone augmentation material 1002 under Kyphoplasty procedure. FIG. 10*b* shows an AP X-ray image of the T11 vertebra filled with the bone augmentation material (1004, 1006) under Kyphoplasty procedure. FIGS. 10*c* and 10*d* show cross-sections of a vertebra injected with the bone augmentation material (1008, 1010, 1012, 1014) (white areas at the bottom of the vertebra, marked with arrows).

As can be seen in the images, the bone augmentation material of the present invention completely filled the bone without leaking else in the bone.

Exemplary Procedure without Active Curing

In some embodiments, the curing process does not require an active curing action, like active use of heat or active use of UV. In some embodiments, the curing is performed using the natural body temperature of the body of the patient. In some embodiments, the whole bone augmentation material is cured, meaning no un-cured bone augmentation material remains in the body. In some embodiments, the bone augmentation material is kept in temperatures that are lower than the average temperature of a healthy person, for example: lower than 37° C. or lower than 36° C., or lower than 30° C. Optionally, from about 0° C. to about 30° C.; optionally from about −8° C. to about 20° C.; optionally from about −20° C. to about 8° C.; optionally lower than −20° C.

This embodiment could be advantageous since the material has no liquid phase all over the procedure, it is a solid also before the curing, therefore eliminates the risk of leakage. Furthermore, another possible advantage of the bone augmentation material of the present invention is that, in some embodiments, no additional external curing means are required. Another possible advantage of the bone augmentation material of the present invention is that no un-cured whole bone augmentation material remains in the body, since the temperature of the body itself is the source of curing activator.

In some embodiments, optionally, a small amount of heat is applied to the zone where the bone augmentation material is located to help with the process of curing which was activated by the natural body heat of the patient.

Exemplary Delivery Methods

In some embodiments, optionally, saline is injected into the bone filler device to reduce friction between the bone augmentation material and the delivery device when the plunger pushes the bone augmentation material.

In some embodiments, optionally, the internal surface of the delivery device is coated, for example with hydrogel materials, polymer coatings and/or hygroscopic salt to reduce friction between the bone augmentation material and the delivery device when the plunger pushes the bone augmentation material. In some embodiments the hydrogel is based on cross-linked Pv-GMA and/or polyacrylate and/or polyvinyl alcohol and/or calcium alginate.

Figure 11:
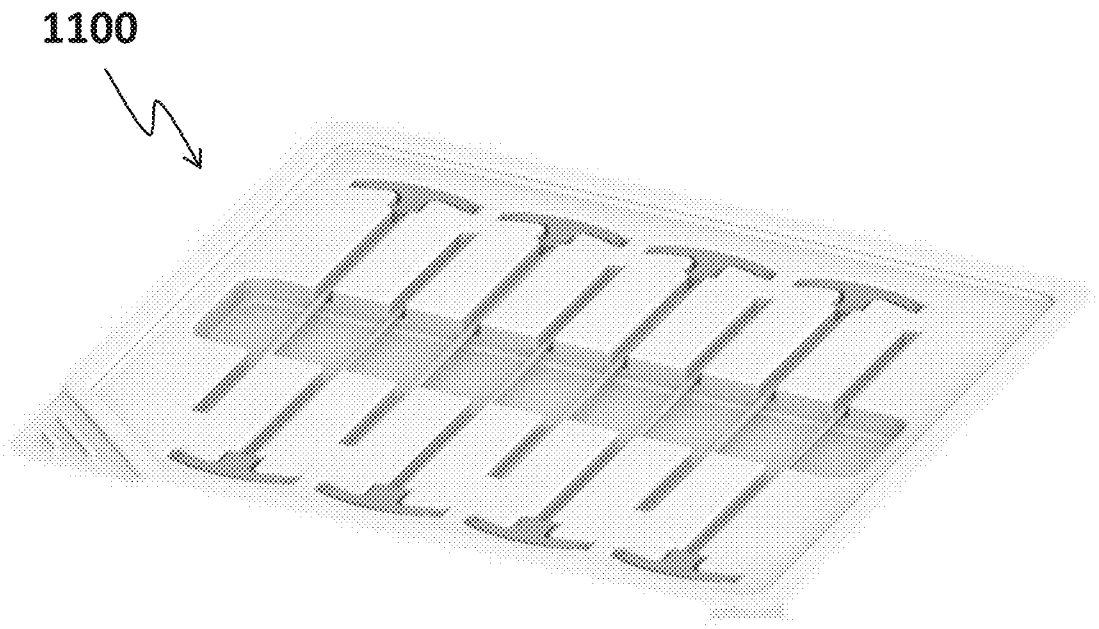
FIG. 11 is a schematic representation of a plurality of pre-filled delivery devices provided in a dedicated sealed sterile blister or tray, according to some embodiments of the present invention.

In some embodiments, optionally, a plurality of pre-filled delivery devices are provided in a dedicated sealed sterile blister or tray 1100, as shown for example in FIG. 11. In some embodiments, optionally, instead of the simple plunger-type delivery system, the injection mechanism is a mechanical or hydraulic mechanism. In some embodiments, the injection mechanism, either simple or mechanical, is adapted to deliver up to 3 cc, or optionally up to 5 cc, or optionally up to 10 cc of the bone augmentation material.

General Exemplary Medical Applications

In some embodiments, the biocompatible bone augmentation material, having the ability to harden following initiation, is used in various applications in the medical field. In some embodiments, each of the following applications comprises a potential advantage over state of the art solutions.

Below are several examples within the medical field, where the implant can be used. The examples below are provided for a human body, but it is clear that any of the following can be implemented on animals too.

Bone Filler

Lack of bone material due to osteoporosis, cancer, or injury, can be filled with the bone augmentation material. Since it is a flexible solid before fixation, it can be easily shaped to fit the target location, placed and fixated only when the desired results are obtained.

Screws Internal Fixation

Screws in weak bones are unstable and may be released. In some embodiments, the bone augmentation material can be transferred through a cannulated screw to fill and strength the bone surrounding the screw, thus fixating the screw without fear of leakage.

Figure 12A:
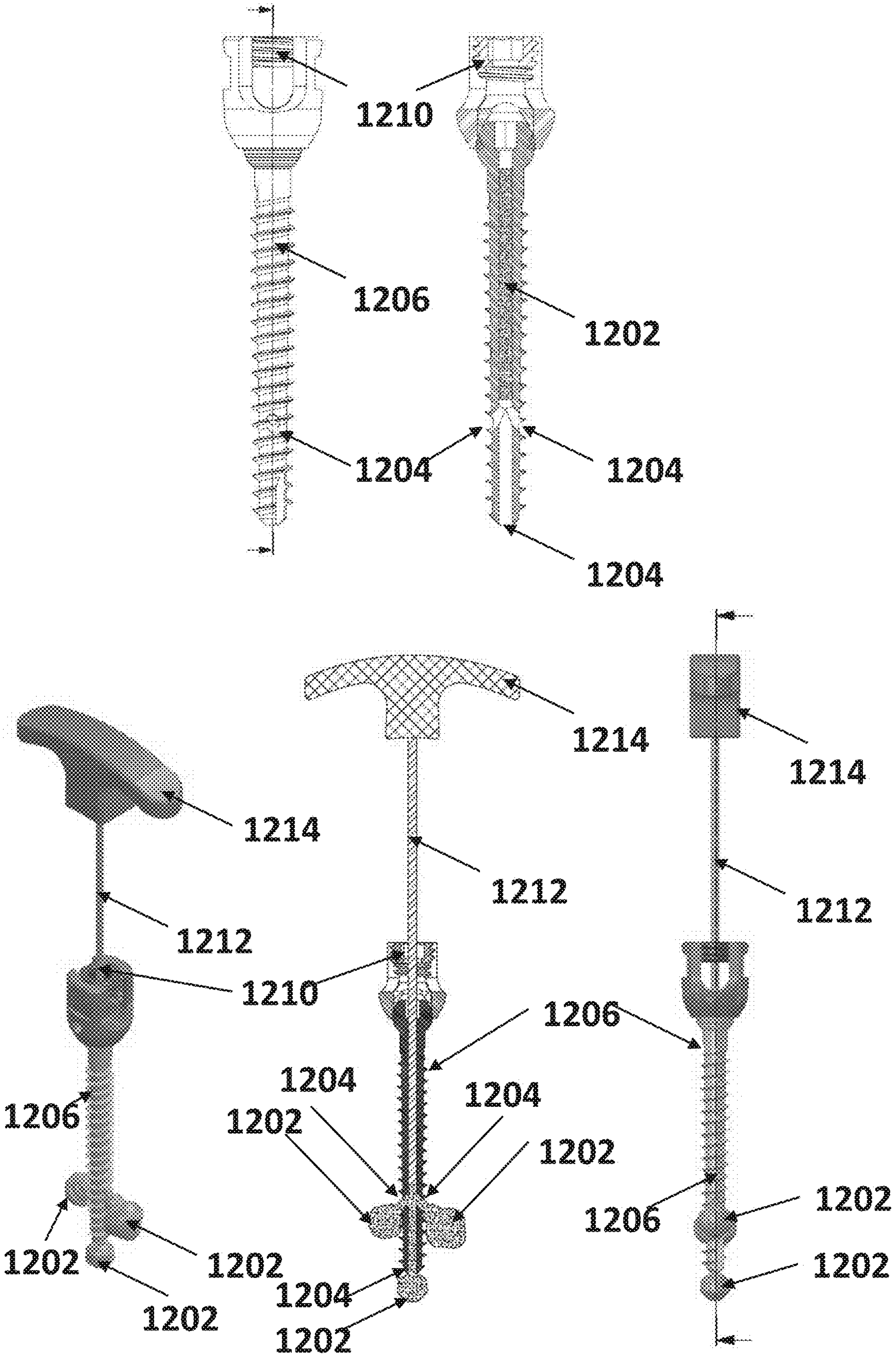
FIGS. 12*a-b* are schematic representations of exemplary embodiments of use of bone augmentation material with orthopedic devices, according to some embodiments of the present invention.
Figure 12B:
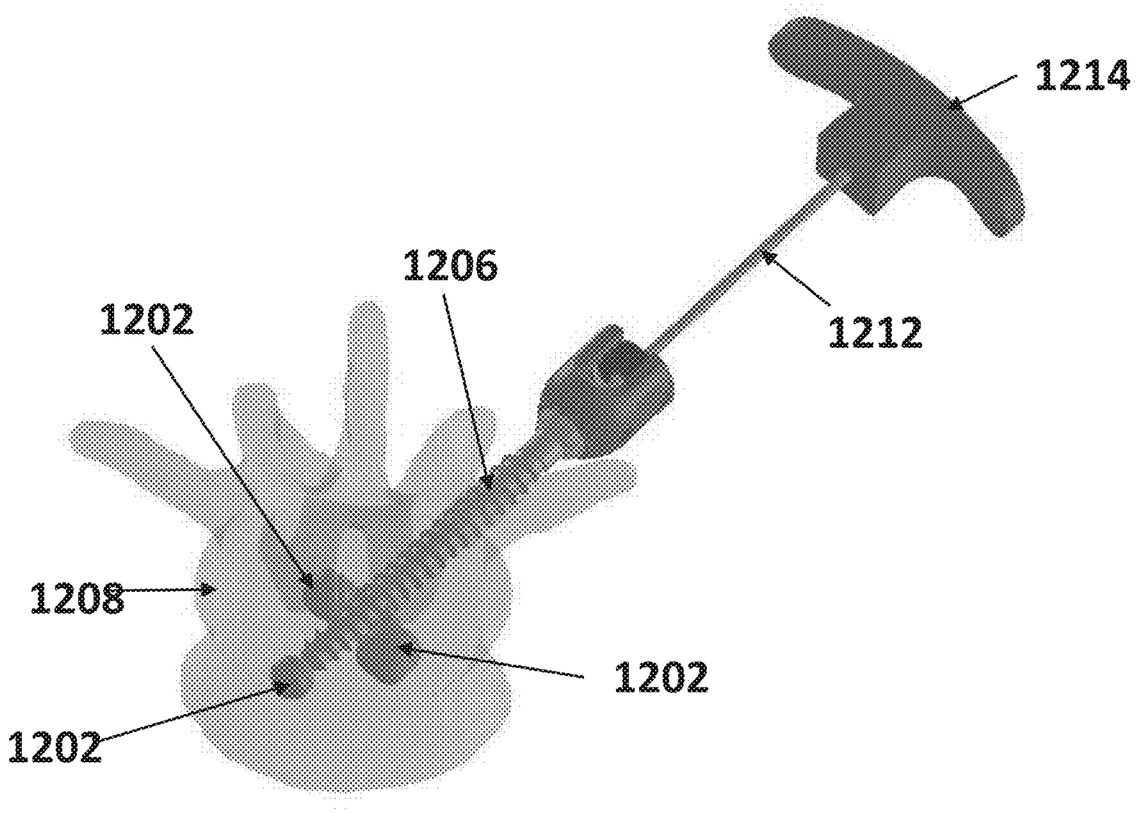

Referring now to FIGS. 12*a*-12*b*, showing an embodiment where the bone augmentation material 1202 is transferred through at least one orifice 1204 (in this case 3 are shown) in the screw 1206 to fill and strength the bone 1208 surrounding the screw 1206. In some embodiments, similarly to the mechanisms previously disclosed, the screw 1206 comprises a proximal opening 1210 where the plunger 1212 comprising a handle 1214 is inserted. In some embodiments, as can be seen, once the plunger 1212 is pushed, the bone augmentation material 1202 exits through the orifices 1204.

Figure 13:
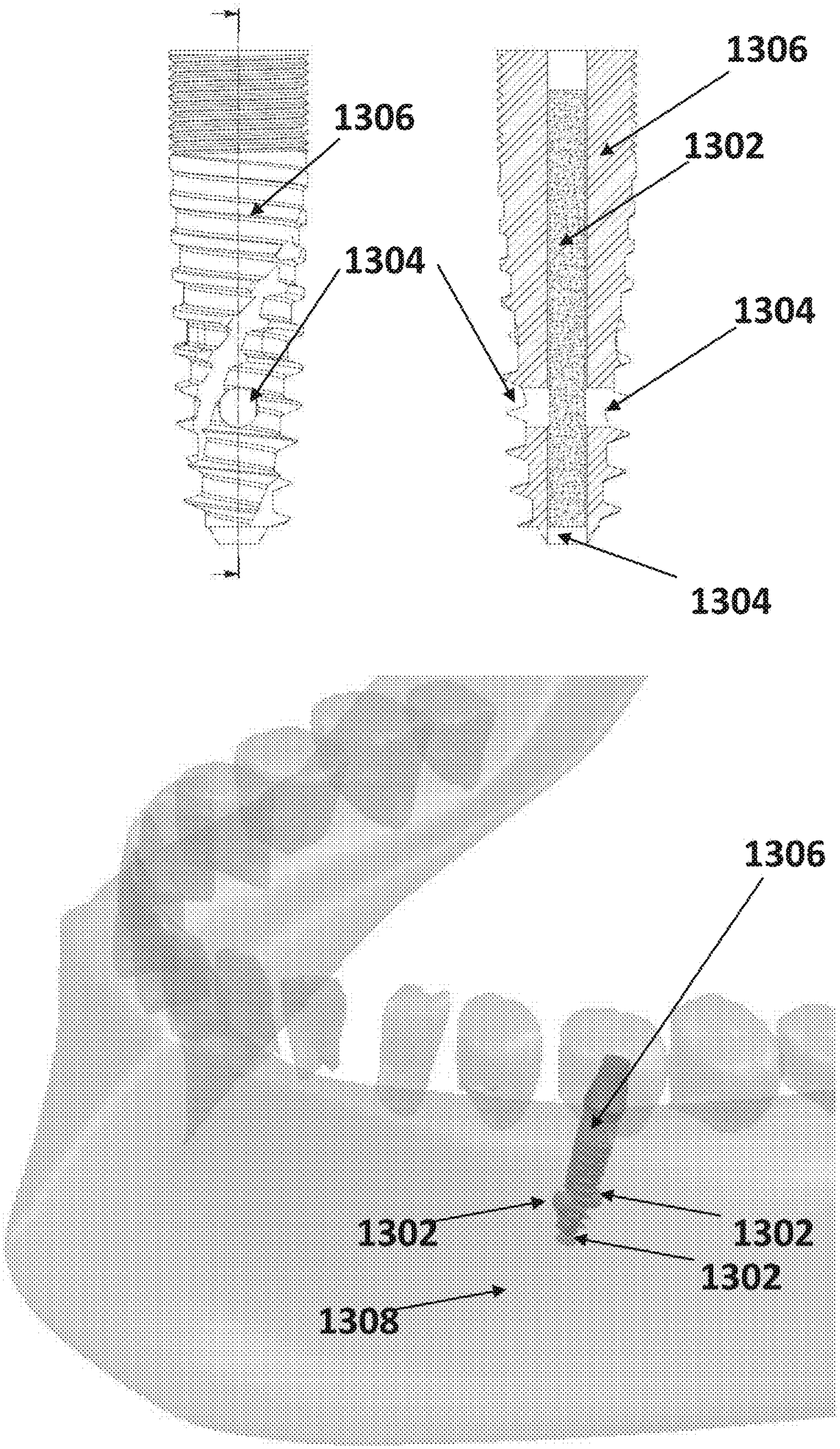
FIG. 13 shows schematic representations of exemplary embodiments of use of bone augmentation material with dental devices, according to some embodiments of the present invention.

Referring now to FIG. 13, showing an embodiment where the bone augmentation material 1302 is transferred through at least one orifice 1304 (in this case 3 are shown) in the dental implant 1306 to fill and strength the bone 1308 surrounding the dental implant 1306.

In some embodiments, while using, for example, medical metal fixators (or screws, or any other orthopedic device) into tissues of patients, the user may locate the metal fixator, apply the bone augmentation material, and meanwhile the bone augmentation material polymerizes, the user may still manipulate the exact location of the metal fixator. In some embodiments, the user cannot manipulate the metal fixator after 40% of the bone augmentation material has been polymerized, optionally after 60%, optionally after 80%, optionally any interval percentage, any higher percentage or any lower percentage. In some embodiments, the user cannot manipulate the metal fixator after 1 minute, optionally after 5 minutes, optionally after 10 minutes, optionally any interval of minutes, any higher number of minutes or any lower number of minutes.

3D Printing Material

Figure 14:
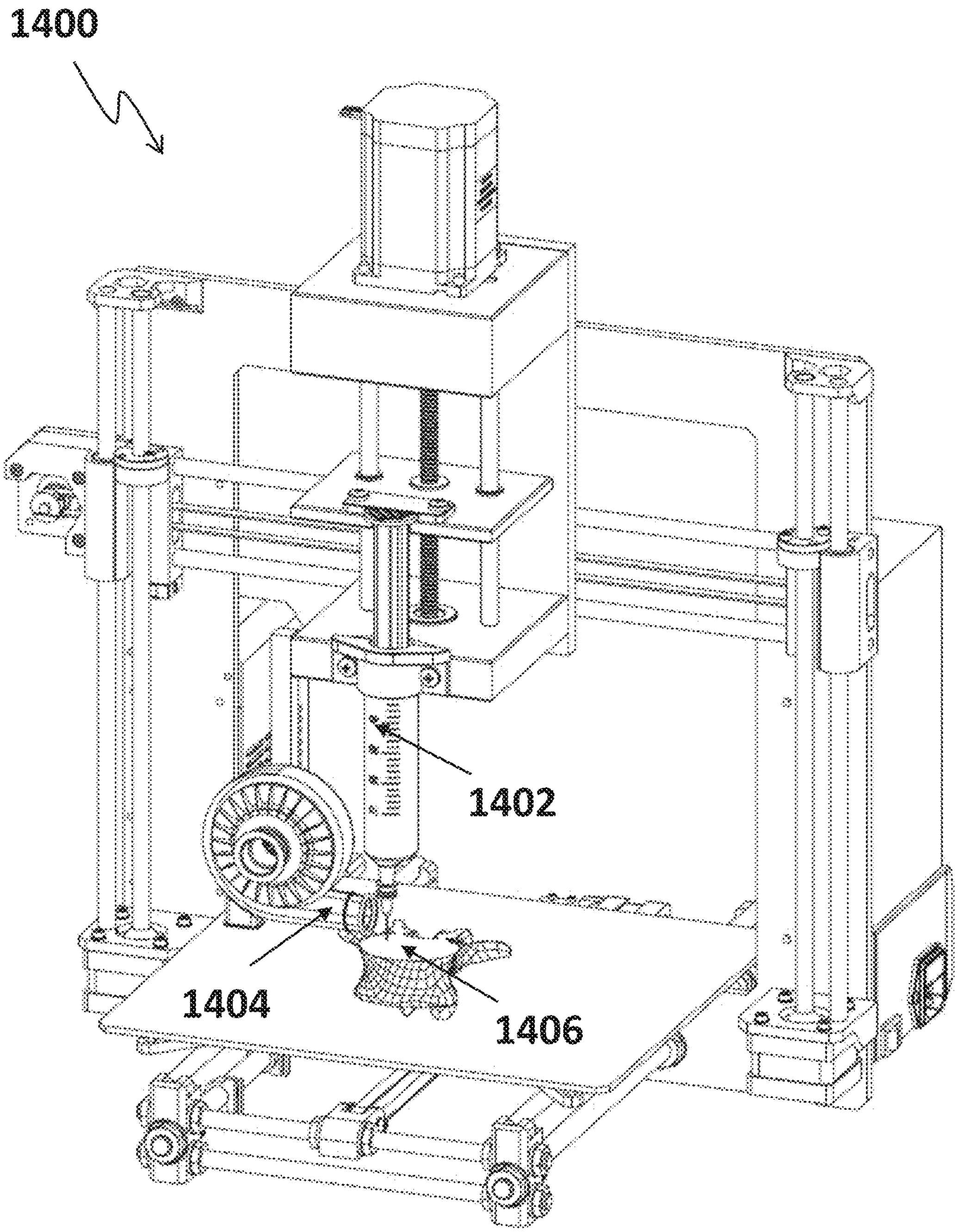
FIG. 14 is a schematic representation of an exemplary 3D printer injector of bone augmentation material, according to some embodiments of the present invention.

Before curing, the bone augmentation material can be immersed in volatile solvent as Acetone or others. Injecting the solution through a suitable 3D printer injector while evaporating the solvent, enables printing of 3D structures made of the polymer, as can be seen for example in FIG. 14, which shows an exemplary 3D printer injector 1400 of bone augmentation material, according to some embodiments of the present invention. In some embodiments, the exemplary 3D printer injector 1400 of bone augmentation material comprises a container 1402 comprising the bone augmentation material (which cannot be seen in FIG. 14). In this example, the container is in the form of a syringe. In some embodiments, the container 1402 includes a liquid form of the bone augmentation material, optionally comprising additives (e.g. such as initiator molecule, radiopaque molecules, growth factors, pharmaceuticals, chemicals, proteins, and others), dissolved, for example, in acetone or any other material. In some embodiments, the exemplary 3D printer injector 1400 comprises means for evaporating the solvent 1404 (in this example, the acetone), for example, an air blower. In some embodiments, other means are used to control the curing process of the bone augmentation material, for example, means to control the temperature of the bone augmentation material. In this example, the printed created a vertebra 1406 for implantation. In some embodiments, this method can be used to produce custom implants with flexibility that allows easy placement and fixation to stiff mater after placement. In some embodiments, the final curing is performed only after implantation of the implant.

Exemplary Connection to Known Delivery Devices

Figure 15:
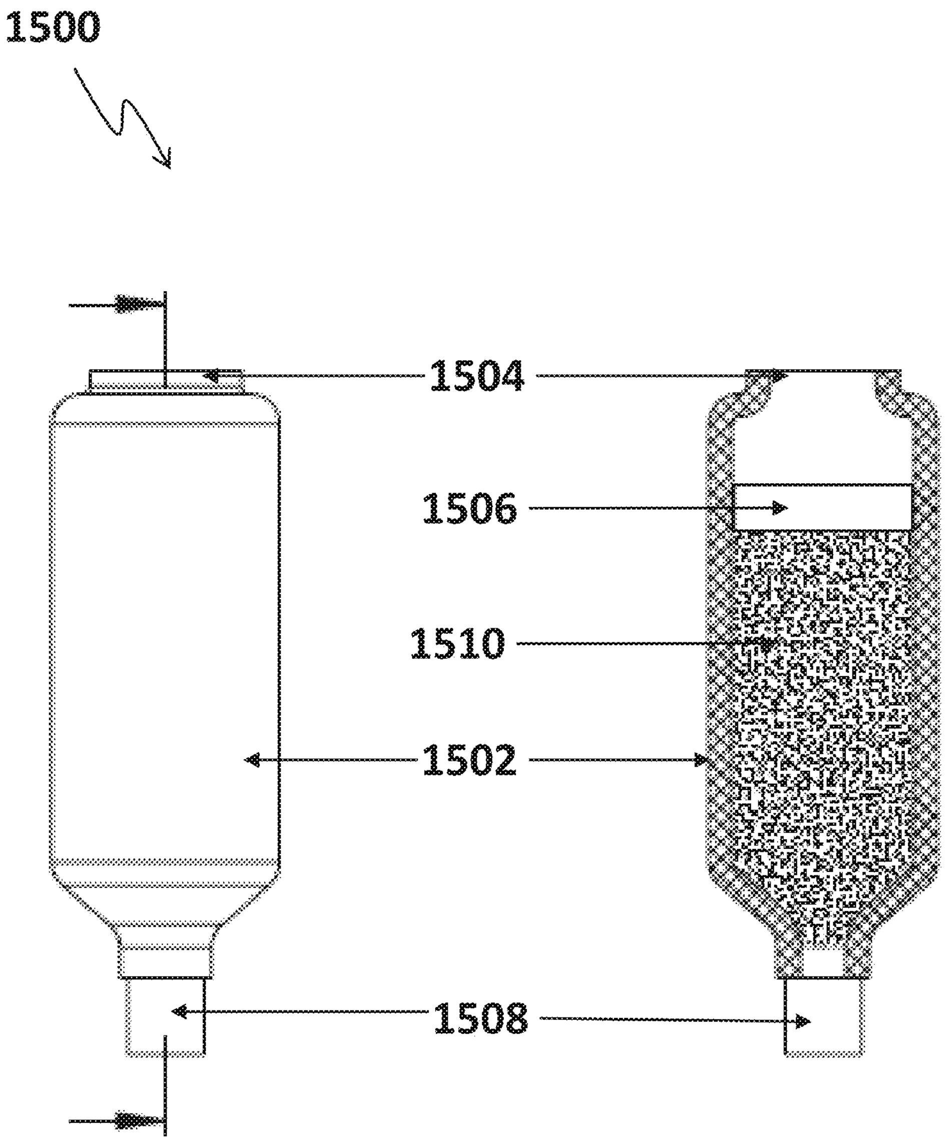
FIG. 15 is a schematic representation of an exemplary cartridge adapted to be connected to a hydraulic system, according to some embodiments of the invention.

Referring now to FIG. 15, showing an exemplary cartridge adapted to be connected to a hydraulic system, according to some embodiments of the invention. In some embodiments, the medical grade implant material 1410 is inserted in a dedicated cartridge 1500 adapted to be connected to a hydraulic system. In some embodiments, the cartridge 1500 comprises a body 1502 comprising a connector 1504 to the hydraulic system at a proximal end of the body 1502, a piston 1506 located inside the body 1402 and a plug 1408 located at the distal end of the body 1402. In some embodiments, when the hydraulic system is activated, the pressure pushes the piston 1506, which causes the medical grade implant material 1410 to exit through the distal end of the cartridge 1500.

General Exemplary Non-Medical Applications

In some embodiments, the materials used as medical grade implants are used in non-medical applications. In some embodiments, the materials are non-medical graded materials. The methods described before apply also here.

Some non-limiting examples of non-medical use are: void filling for construction or aviation (where a lightweight material is needed), gluing substitutes anchoring (screw anchor), art, crafting, prototypes fabrication, temperature isolation and fluids filtration.

It is expected that during the life of a patent maturing from this application many relevant methods will be developed.

As used herein with reference to quantity or value, the term "about" means "within ±25% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A medical grade implant, comprising a deformable body formed of at least 20% by volume of a polymer material in which individual polymer backbones have a plurality of functional groups capable of cross-linking to form a cross-link; said polymer material provided in a first less-cross-linked configuration; wherein said polymer material, upon application of an initiator, said initiator causes cross-linking of said functional groups to form cross-linking between said polymer backbones such that said polymer material is in a second more-cross-linked configuration;

wherein said initiator is mixed in a mix of viscous paste polymer; and wherein mixing of said initiator with said deformable body is self-mixing and said mixing is achieved during a delivery process.

2. The implant according to claim 1, wherein the polymer comprises methacrylate groups covalently attached to polyvinyl alcohol (PVA).

3. The implant according to claim 1, wherein said functional groups comprise methacrylate and said polymer backbones comprise PVA.

4. The implant according to claim 1, wherein the polymer is selected from the group consisting of Pv-GMA, Pv-IMA, Pv-AMA, Pv-EMA, Pv-MA, Pv-GMA-GAE, Pv-GMA-AE or any combination thereof.

5. The implant according to claim 1, wherein said implant comprises from about 1% to about 25% of an internal or external plasticizer.

6. The implant according to claim 1, wherein said polymer comprises less than 10% of free monomers.

7. The implant according to claim 1, wherein said polymer comprises no free monomers.

8. The implant according to claim 1, wherein said implant comprises from about 20% to about 90% by volume of said polymer material.

9. The implant according to claim 1, wherein in said first less-cross-linked configuration said implant has an elastic modulus from about 0.01 to about 1 MPa.

10. The implant according to claim 1, wherein in said second more-cross-linked configuration said device has an elastic modulus from about 2 to about 500 MPa.

11. The implant according to claim 10, wherein said elastic modulus changes from said first less-cross-linked configuration to said second more-cross-linked configuration by a factor from about 10 to about 1000.

12. The implant according to claim 1, wherein an average molecular weight of said polymer is from about 1,000 to about 200,000 g/mol.

13. The implant according to claim 1, wherein a natural heat of a patient is configured to be a suitable stimuli for said cross-linking.

14. The implant according to claim 1, wherein said functional groups are active functional groups.

15. The implant according to claim 1, wherein the time required for said cross-linking to finish 80% of the cross-linking is from about 1 minutes to about 60 minutes.

16. The implant according to claim 1, wherein said initiator is a small molecule.

17. The implant according to claim 1, wherein said implant is made of biocompatible materials.

18. The implant according to claim 1, wherein said deformable body comprises at least one pharmacological agent.

19. The implant according to claim 1, wherein said deformable body comprises at least one additional radiopaque marker additive.

20. The implant according to claim 1, wherein said deformable body and said initiator are spatially separated before said application of said initiator.

21. The implant according to claim 1, wherein a natural moisture of a patient is configured to be a suitable stimuli for said cross-linking.

* * * * *